United States Patent
Leigh et al.

(10) Patent No.: US 11,850,417 B2
(45) Date of Patent: Dec. 26, 2023

(54) FEEDTHROUGH PLACEMENT

(71) Applicant: Cochlear Limited, Macquarie University (AU)

(72) Inventors: Charles Roger Aaron Leigh, Macquarie University (AU); Wilson Fung, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1283 days.

(21) Appl. No.: 15/380,523

(22) Filed: Dec. 15, 2016

(65) Prior Publication Data

US 2018/0169410 A1    Jun. 21, 2018

(51) Int. Cl.
| | |
|---|---|
| *A61N 1/375* | (2006.01) |
| *A61N 1/05* | (2006.01) |
| *A61N 1/36* | (2006.01) |
| *A61N 1/372* | (2006.01) |

(52) U.S. Cl.
CPC ....... *A61N 1/0541* (2013.01); *A61N 1/36036* (2017.08); *A61N 1/36038* (2017.08); *A61N 1/3754* (2013.01); *A61N 1/37211* (2013.01); *A61N 1/3758* (2013.01)

(58) Field of Classification Search
CPC . A61N 1/36036; A61N 1/3754; H04R 25/554
See application file for complete search history.

(56) References Cited

U.S. PATENT DOCUMENTS

| | | | |
|---|---|---|---|
| 4,874,910 A | 10/1989 | McCoy | |
| 5,817,984 A * | 10/1998 | Taylor | H01B 17/305 174/152 GM |
| 5,988,507 A | 11/1999 | Ikeda et al. | |
| 6,143,440 A * | 11/2000 | Volz | H01M 50/572 429/92 |
| 6,807,048 B1 | 10/2004 | Nielsen et al. | |
| 7,174,223 B2 | 2/2007 | Dalton et al. | |
| 7,988,507 B2 | 8/2011 | Darley et al. | |

(Continued)

FOREIGN PATENT DOCUMENTS

| | | |
|---|---|---|
| CN | 102671299 A | 9/2012 |
| CN | 103476361 A | 12/2013 |

(Continued)

OTHER PUBLICATIONS

International Search Report and Written Opinion for PCT/IB2017/057222, dated Mar. 13, 2018.

(Continued)

*Primary Examiner* — Michael J D'Abreu
(74) *Attorney, Agent, or Firm* — Piloff Passino & Cosenza LLP; Martin J. Cosenza

(57) ABSTRACT

A device, including a housing of a medical device configured to be implanted in a human recipient, the housing having at least one opening on one side of the housing, and a linear feedthrough assembly, wherein the linear feedthrough assembly closes the opening, the housing has a length, a width, and a height, wherein the height is the smallest dimension, and the opening is located in at least about the center of at least one of the length or the width, and the opening faces a direction normal to a plane established by the length and the width.

27 Claims, 30 Drawing Sheets

(56) References Cited

U.S. PATENT DOCUMENTS

| | | | |
|---|---|---|---|
| 8,515,540 B2 | 8/2013 | Leigh et al. | |
| 8,885,837 B2 | 11/2014 | Darley et al. | |
| 2002/0071581 A1* | 6/2002 | Leysieffer | H04R 25/606 |
| | | | 381/312 |
| 2005/0033377 A1* | 2/2005 | Milojevic | A61N 1/36038 |
| | | | 607/45 |
| 2009/0023976 A1 | 1/2009 | Cho et al. | |
| 2011/0208267 A1 | 8/2011 | Eder et al. | |
| 2011/0297439 A1 | 12/2011 | Talamine et al. | |
| 2012/0016444 A1 | 1/2012 | Koester | |
| 2012/0193118 A1 | 8/2012 | Kempf et al. | |
| 2012/0221078 A1 | 8/2012 | Eigh et al. | |
| 2013/0032391 A1 | 2/2013 | Morioka et al. | |
| 2013/0096366 A1* | 4/2013 | Bervoets | A61N 1/36036 |
| | | | 600/25 |
| 2013/0100595 A1 | 4/2013 | Koester et al. | |
| 2013/0197298 A1* | 8/2013 | Miller | H04R 25/00 |
| | | | 600/25 |
| 2014/0088704 A1 | 3/2014 | Walling et al. | |
| 2015/0087892 A1 | 3/2015 | Tourrel et al. | |
| 2015/0088226 A1 | 3/2015 | Tourrel et al. | |
| 2015/0224312 A1 | 8/2015 | Platz et al. | |
| 2016/0082249 A1 | 3/2016 | Thenuwara et al. | |

FOREIGN PATENT DOCUMENTS

| | | |
|---|---|---|
| CN | 104511091 A | 4/2015 |
| KR | 100859979 B1 | 9/2008 |
| WO | 2006081361 A2 | 8/2006 |
| WO | 2011143266 A2 | 11/2011 |

OTHER PUBLICATIONS

Office action for CN Application No. 201780077788.8, dated Jul. 27, 2020.
Office action for CN Application No. 201780077788.8, dated Jul. 22, 2022.

* cited by examiner

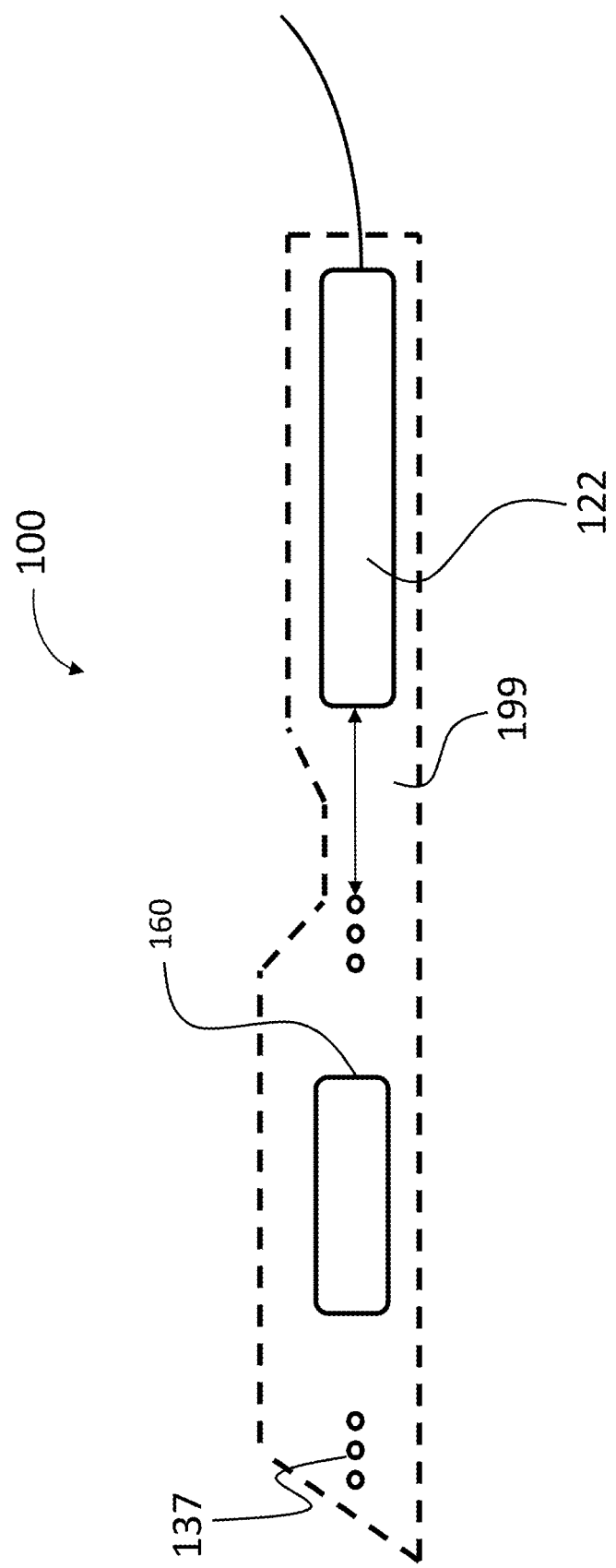

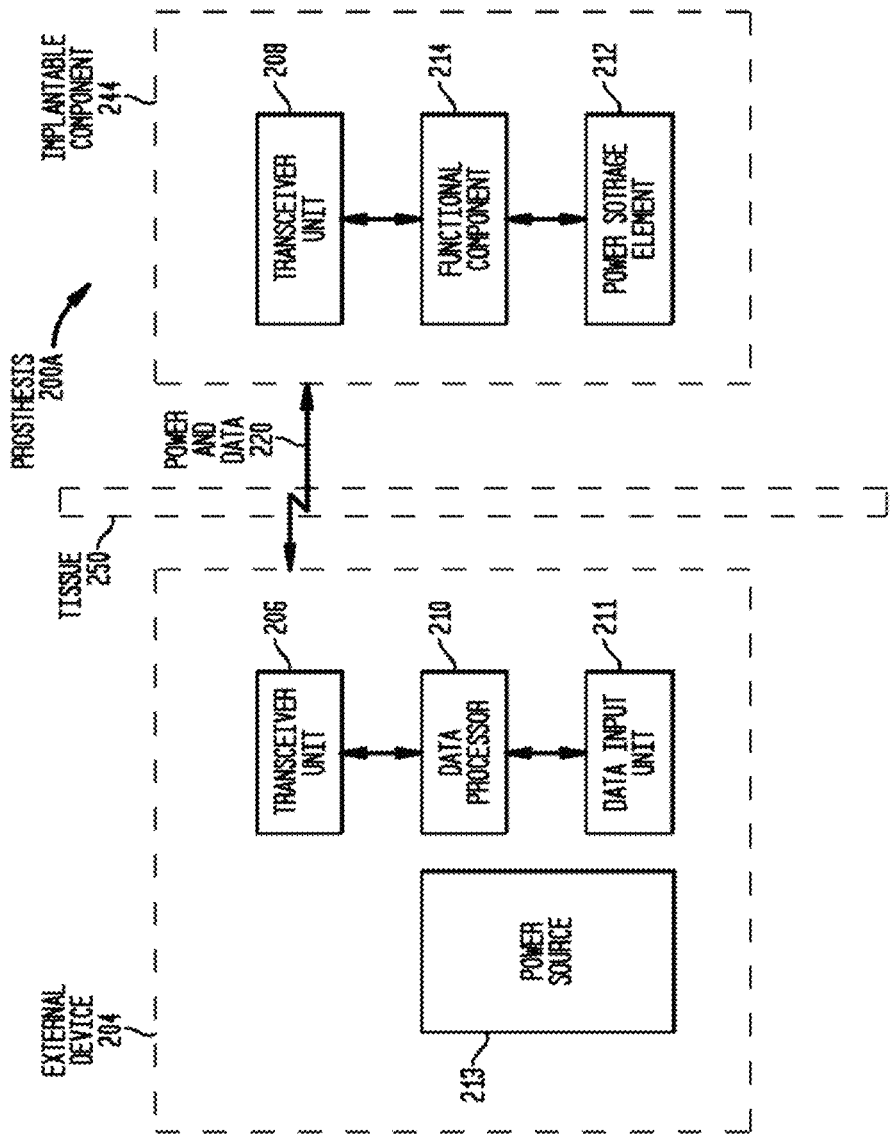

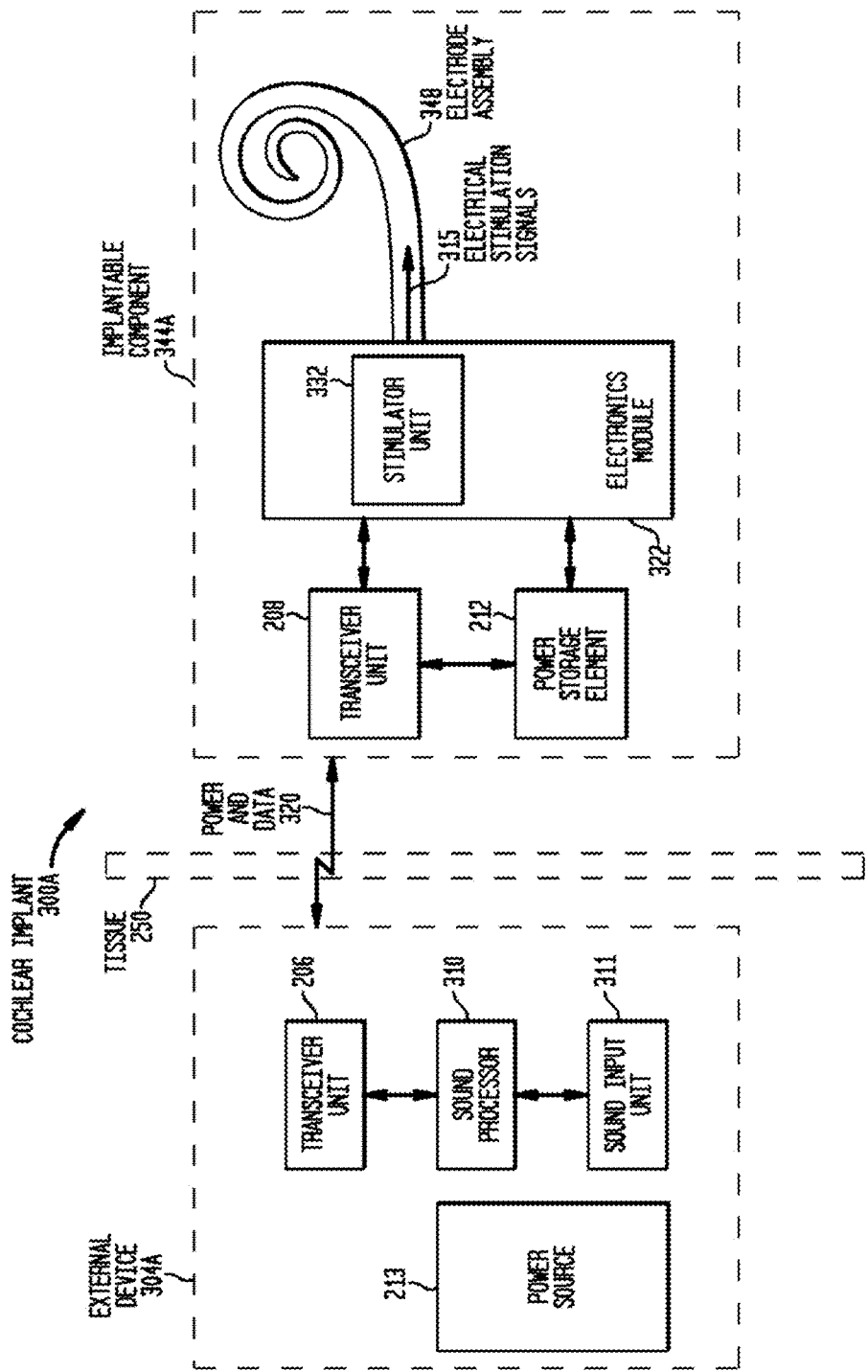

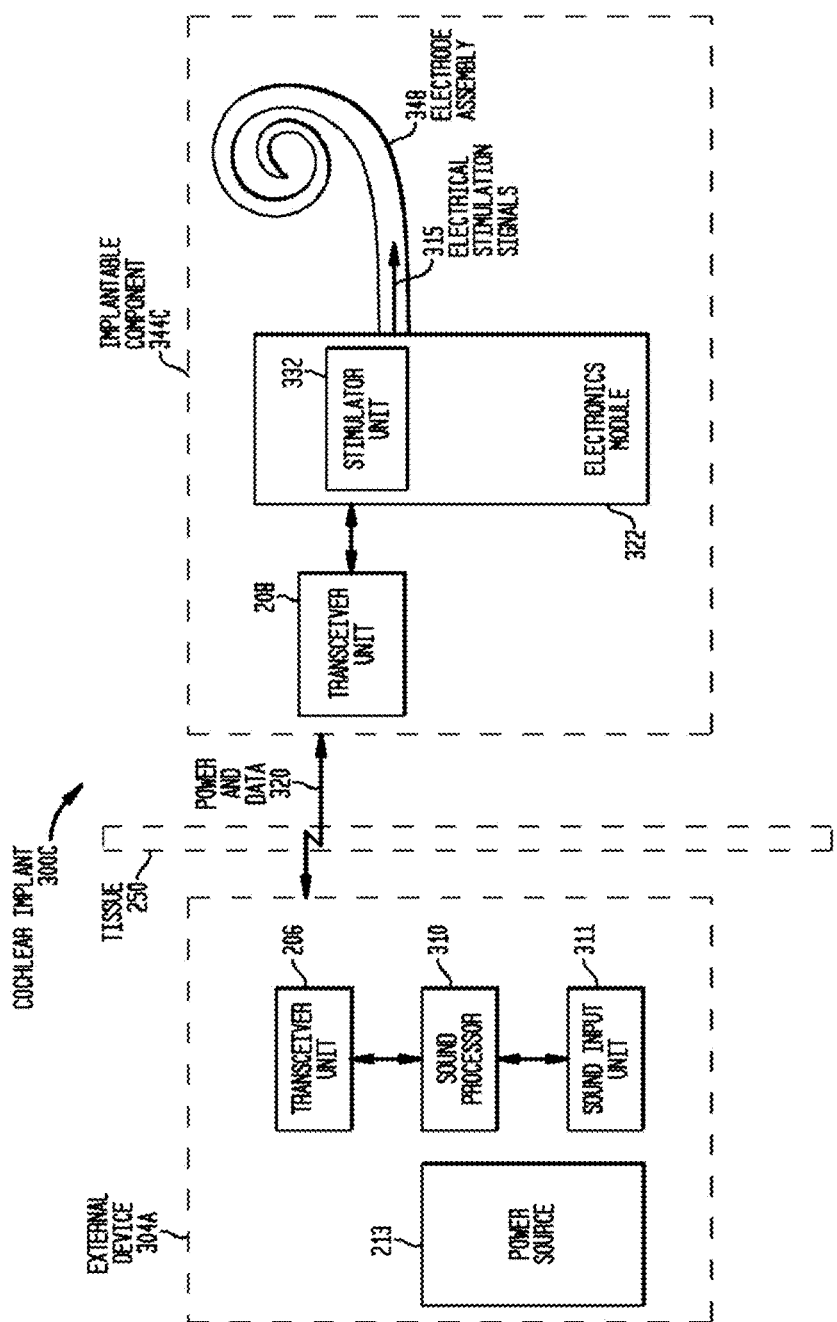

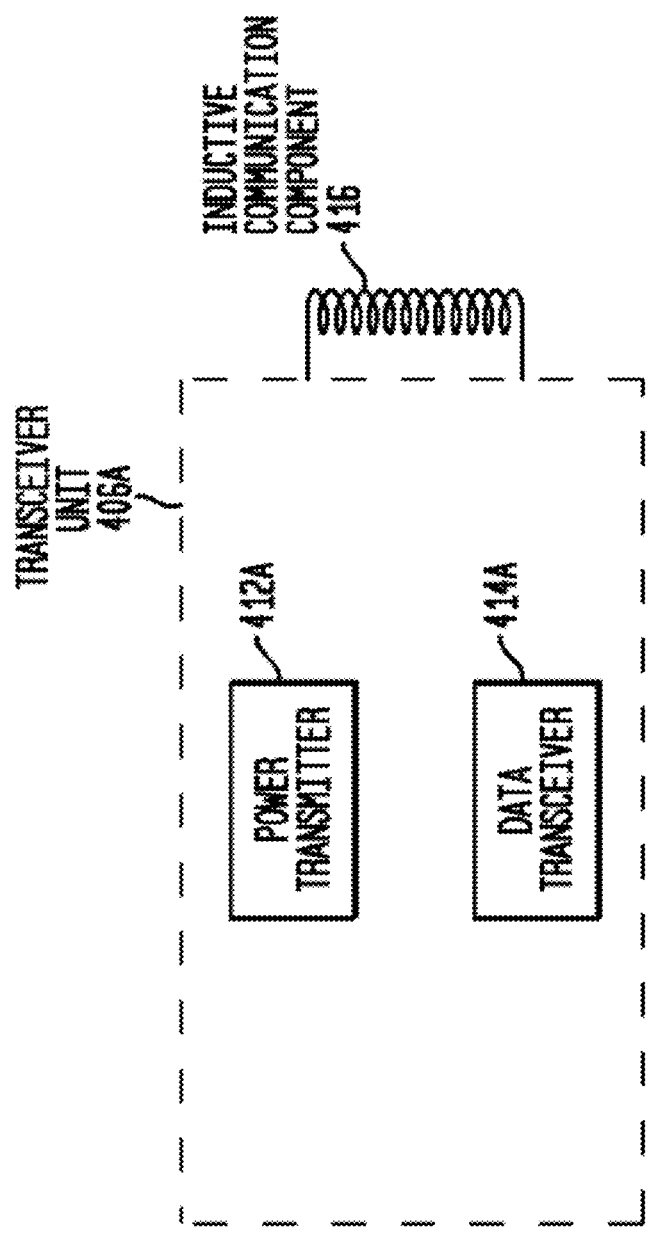

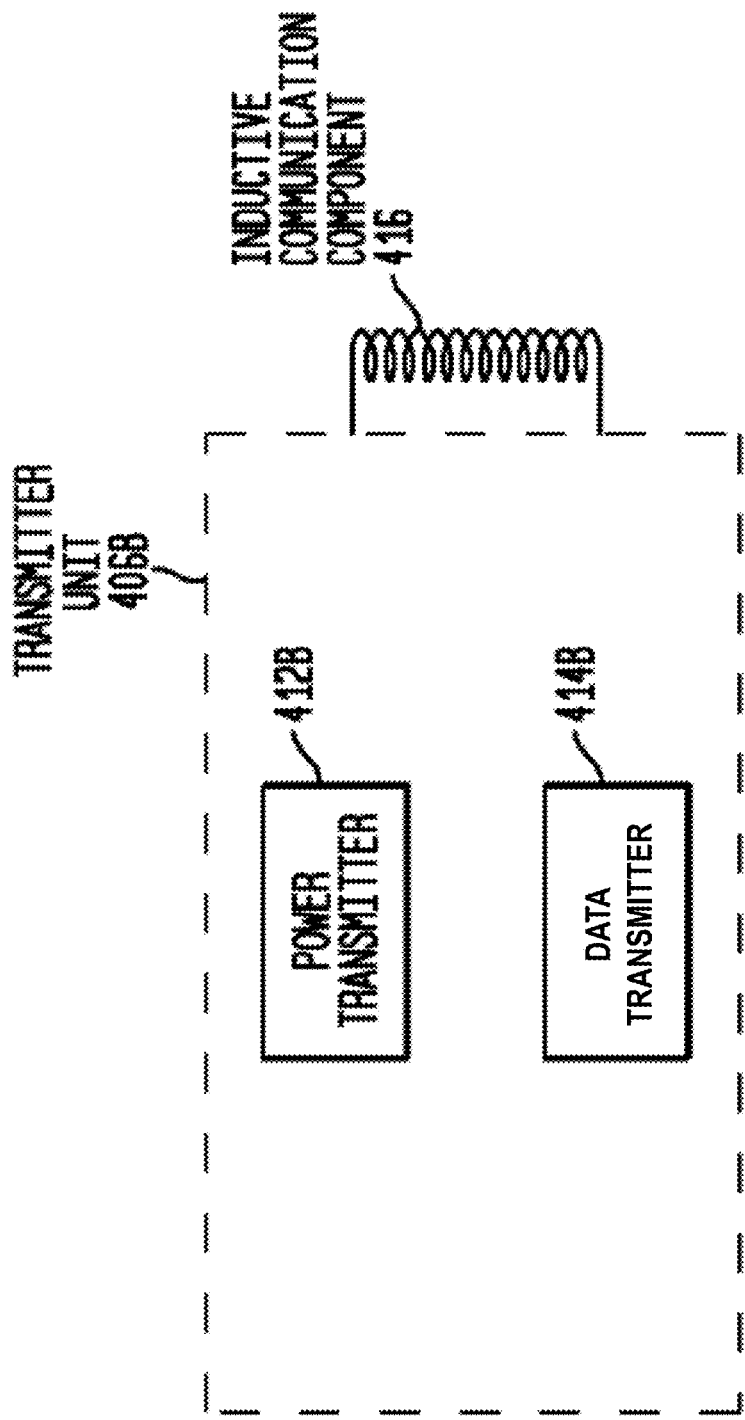

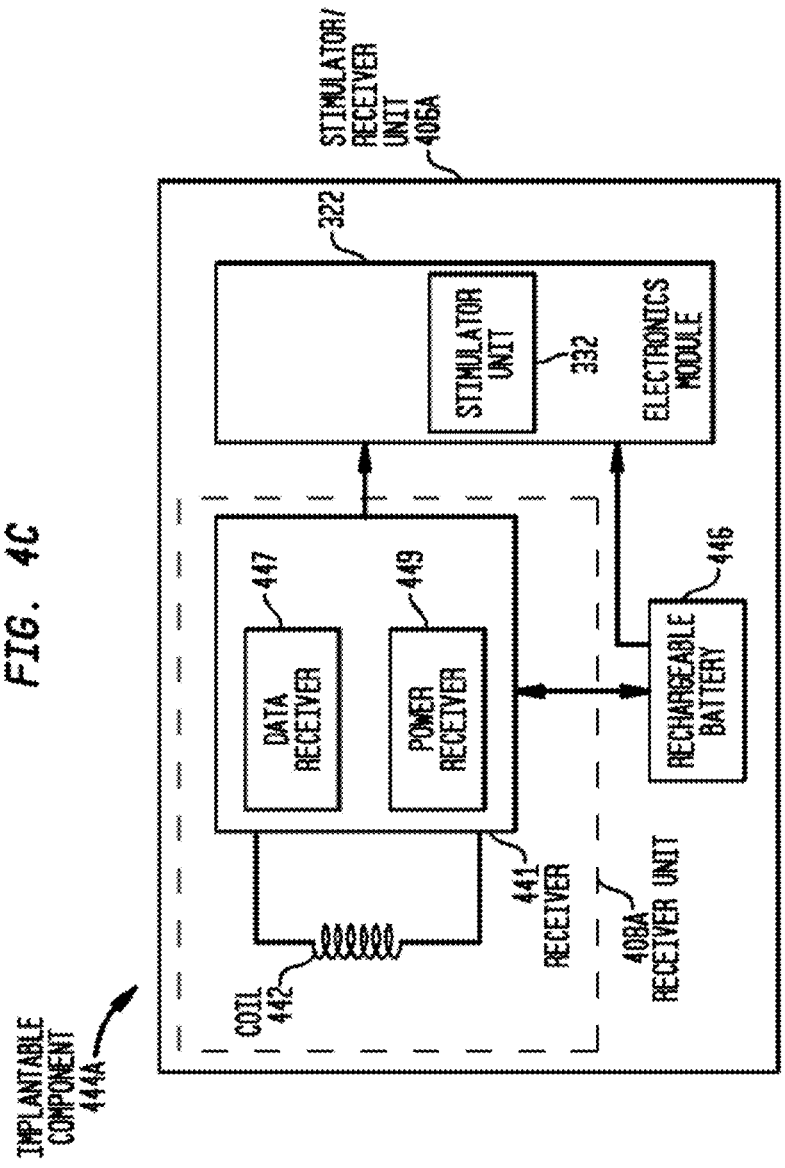

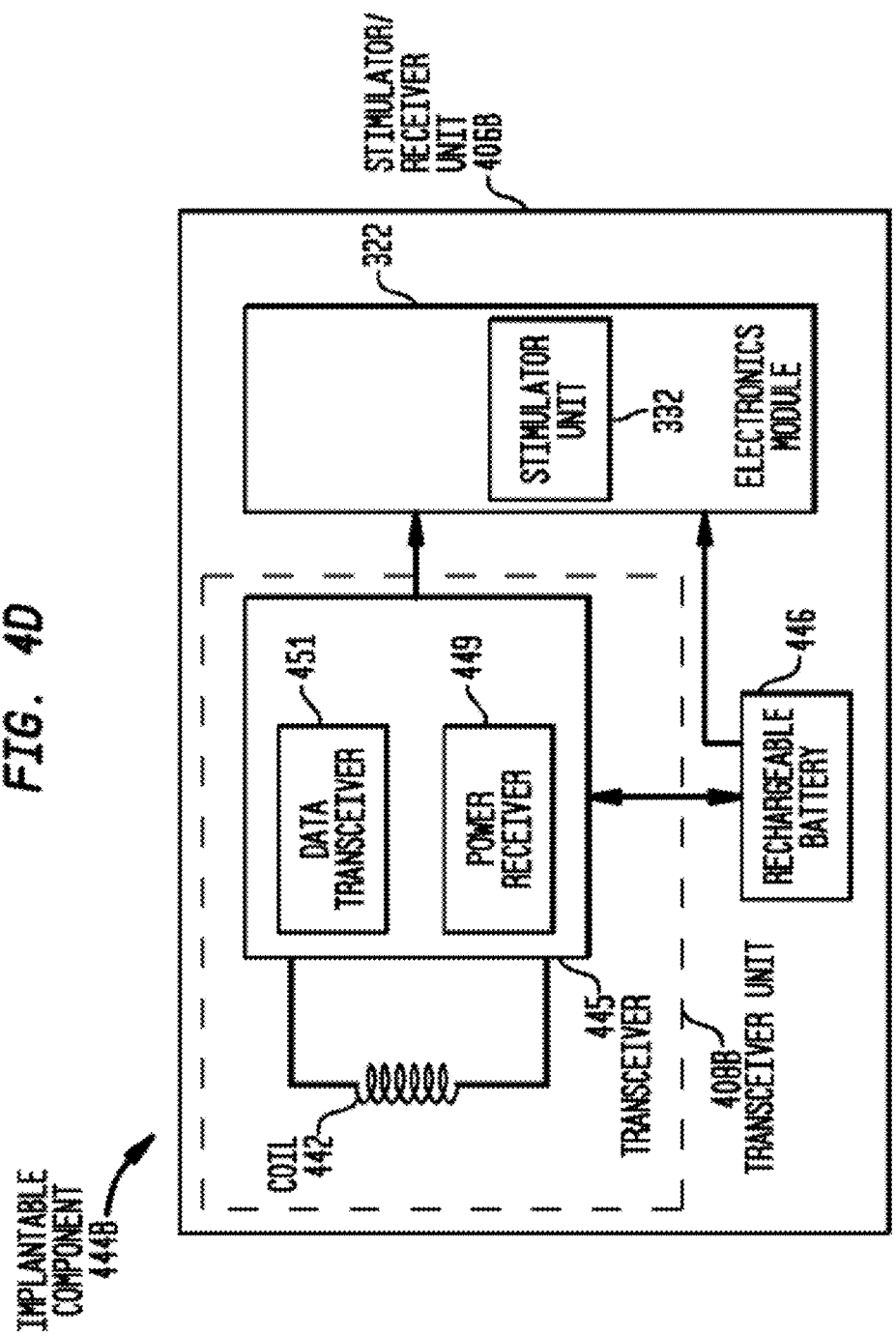

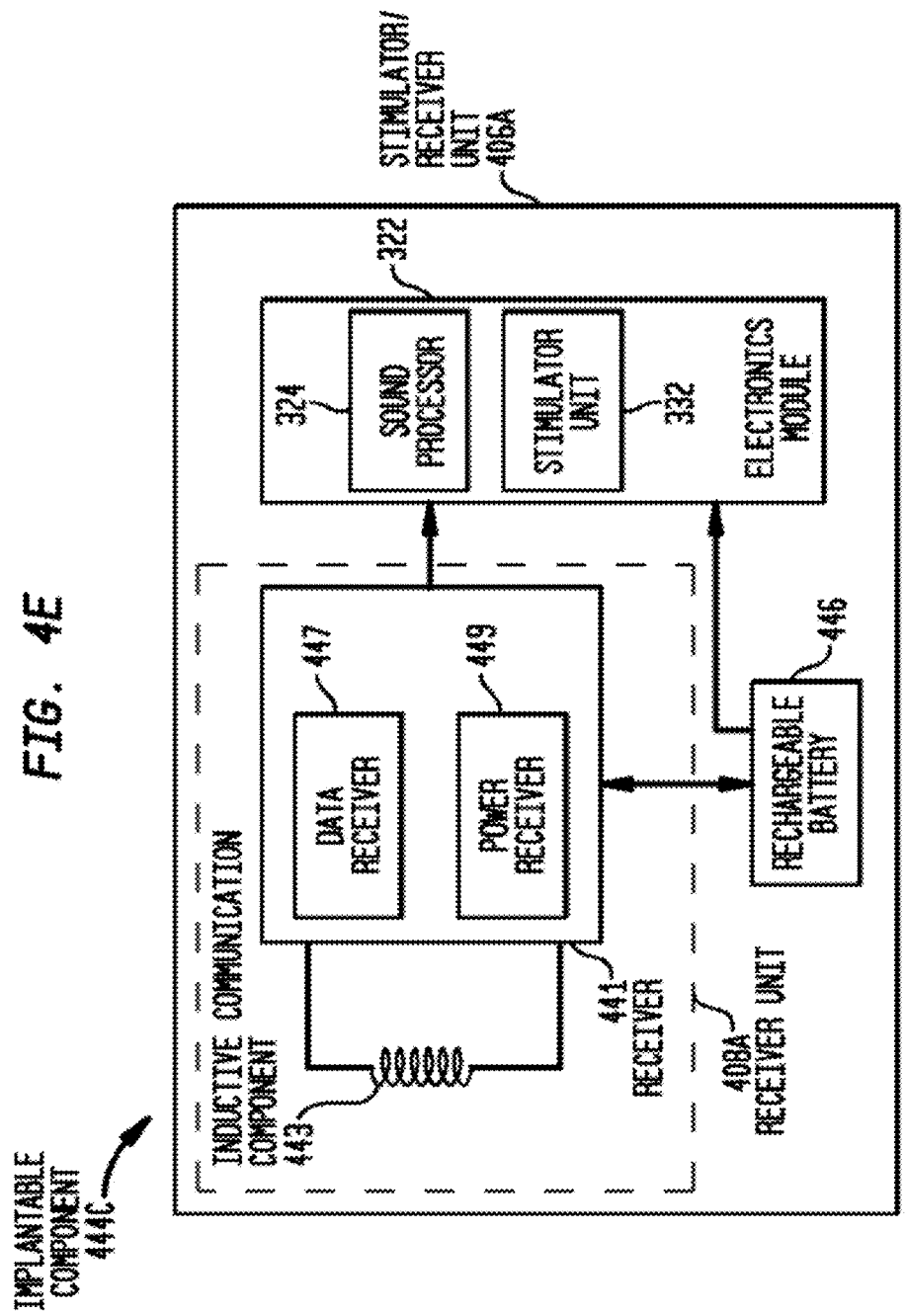

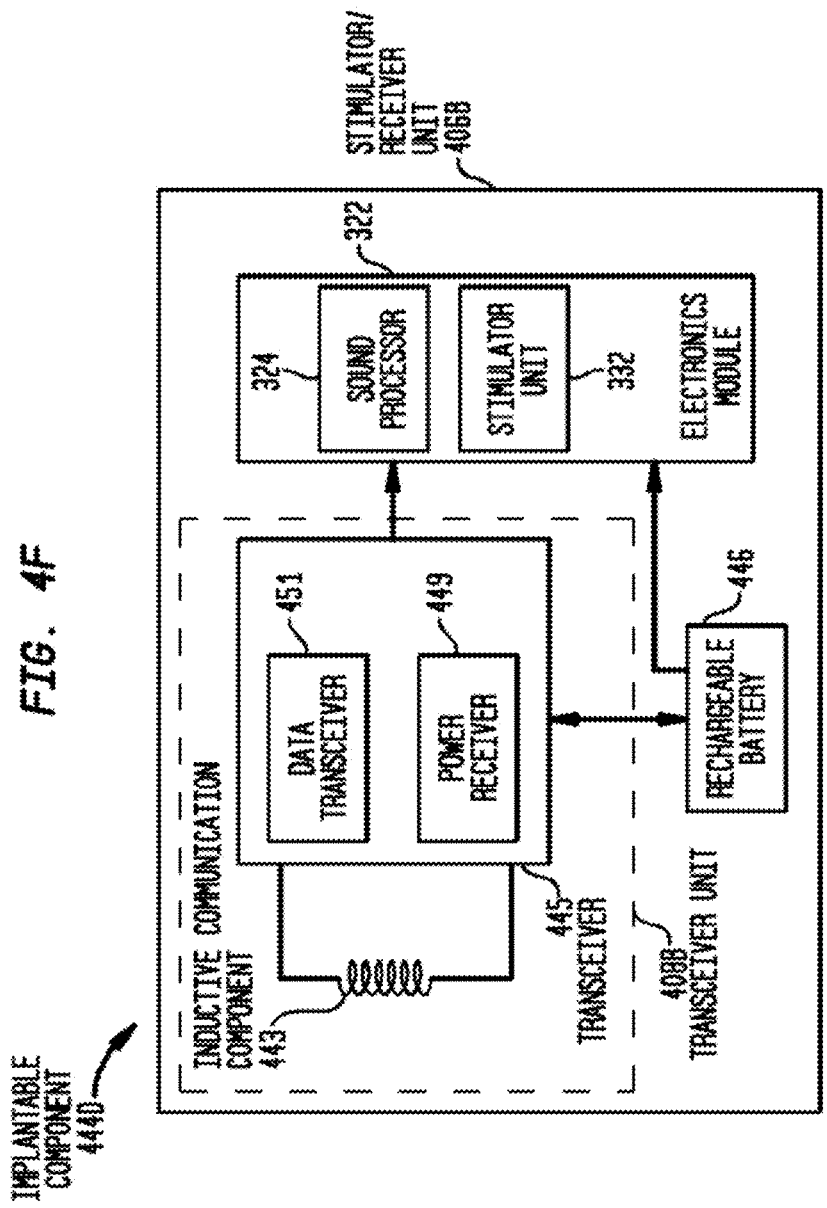

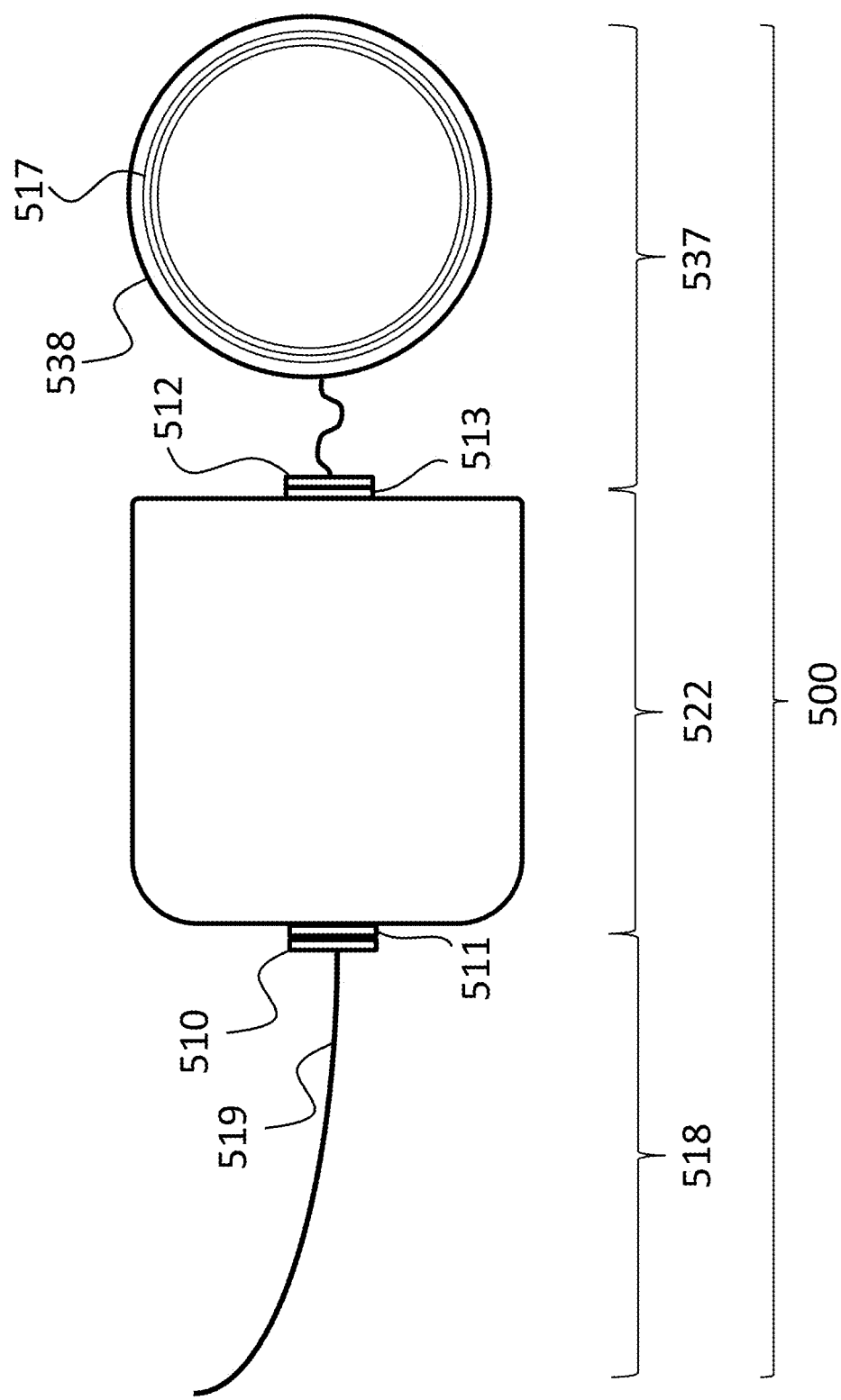

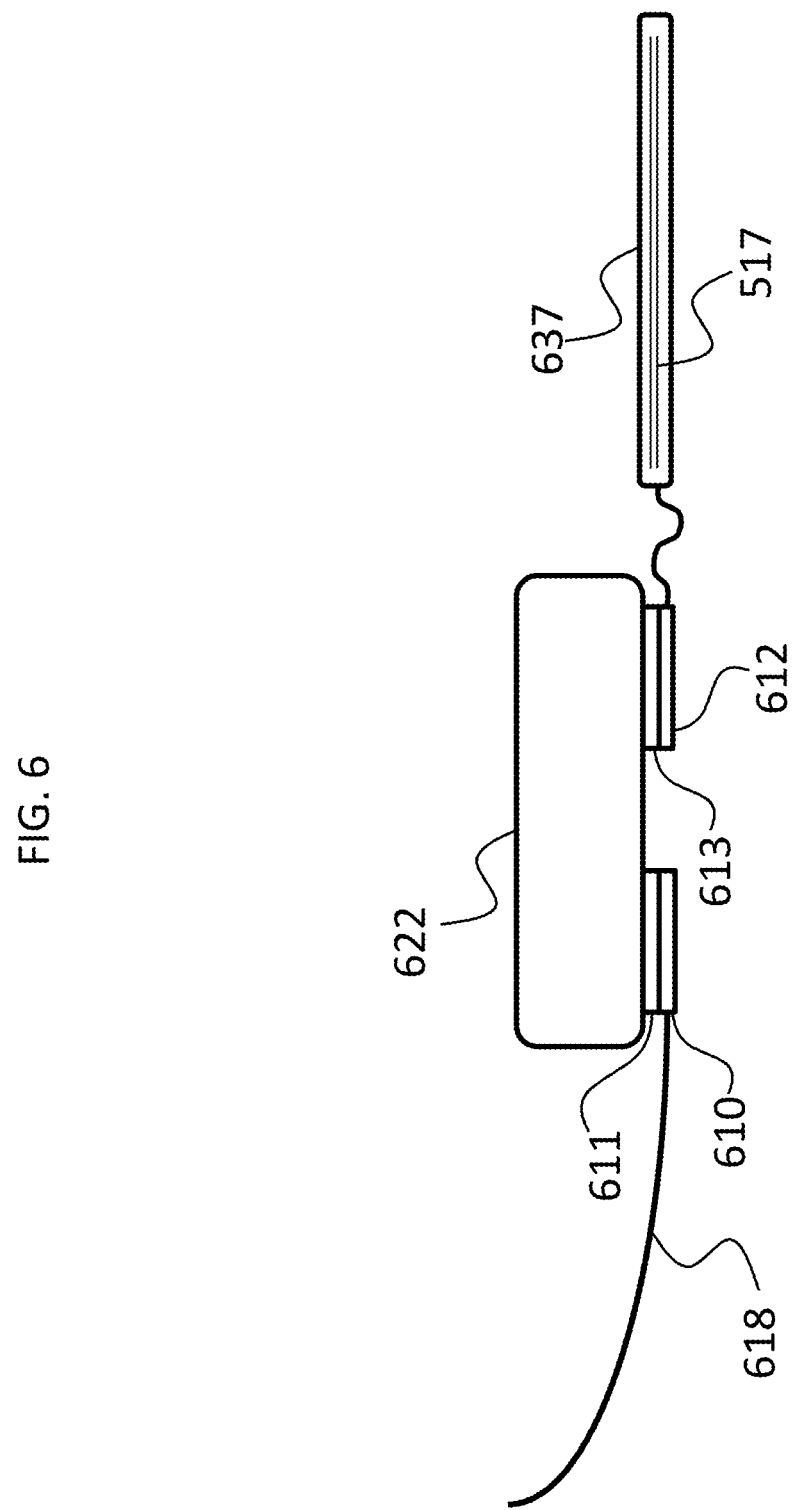

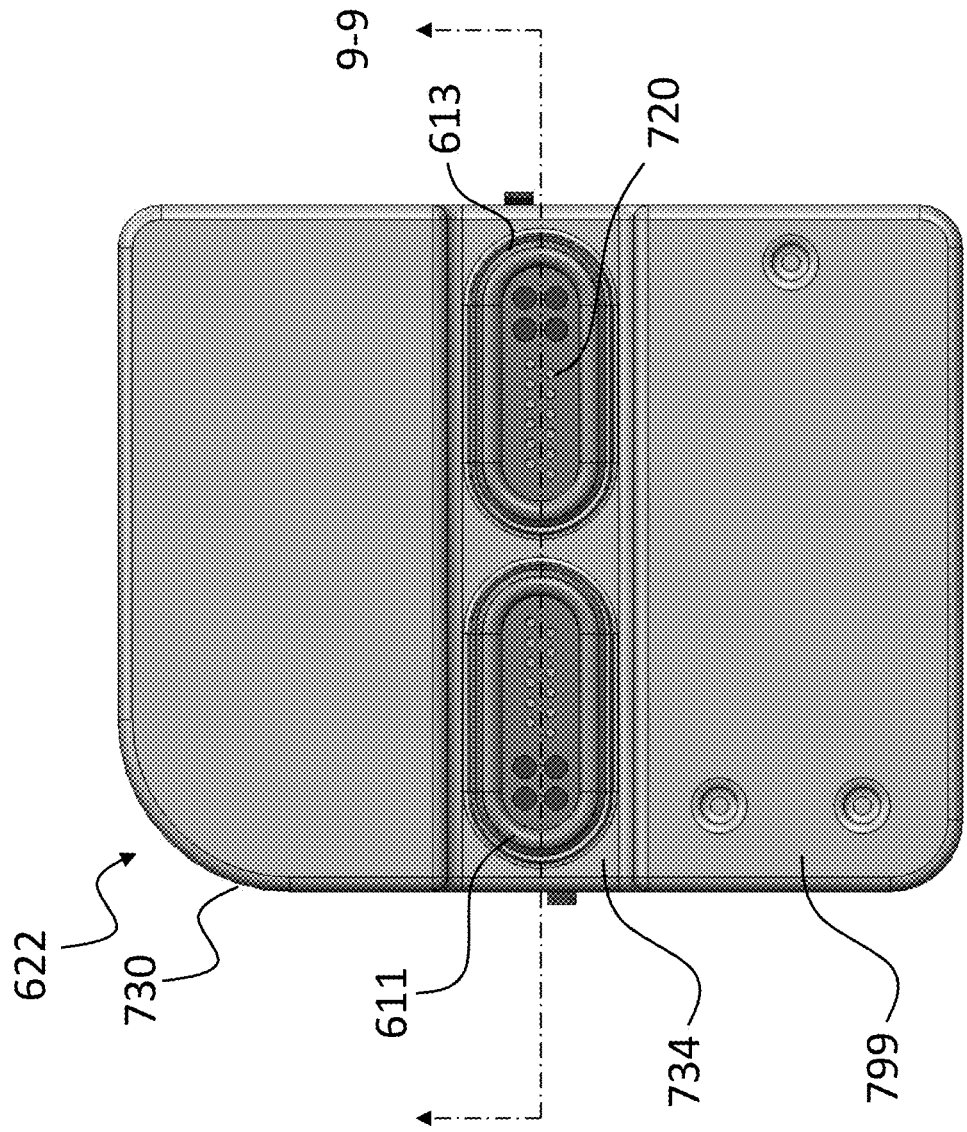

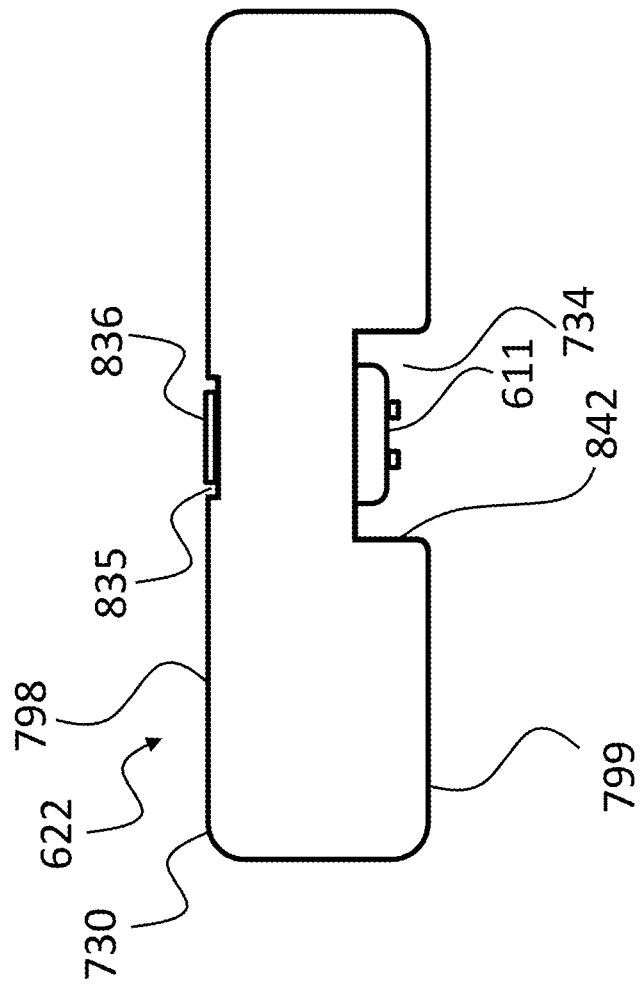

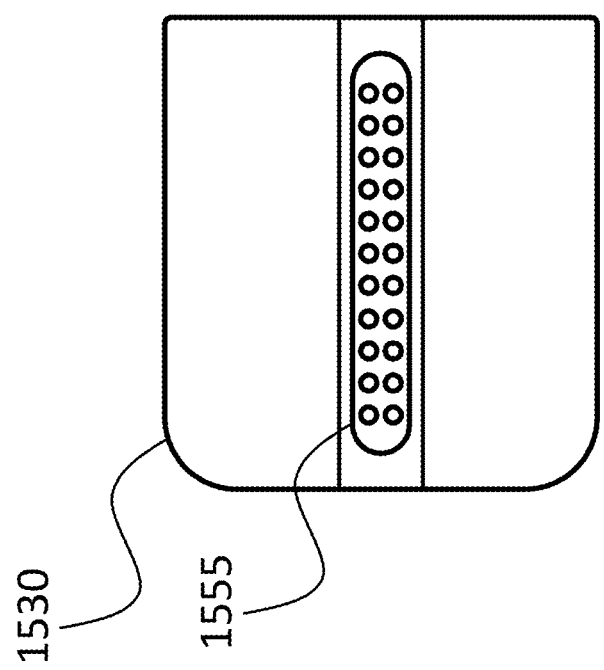

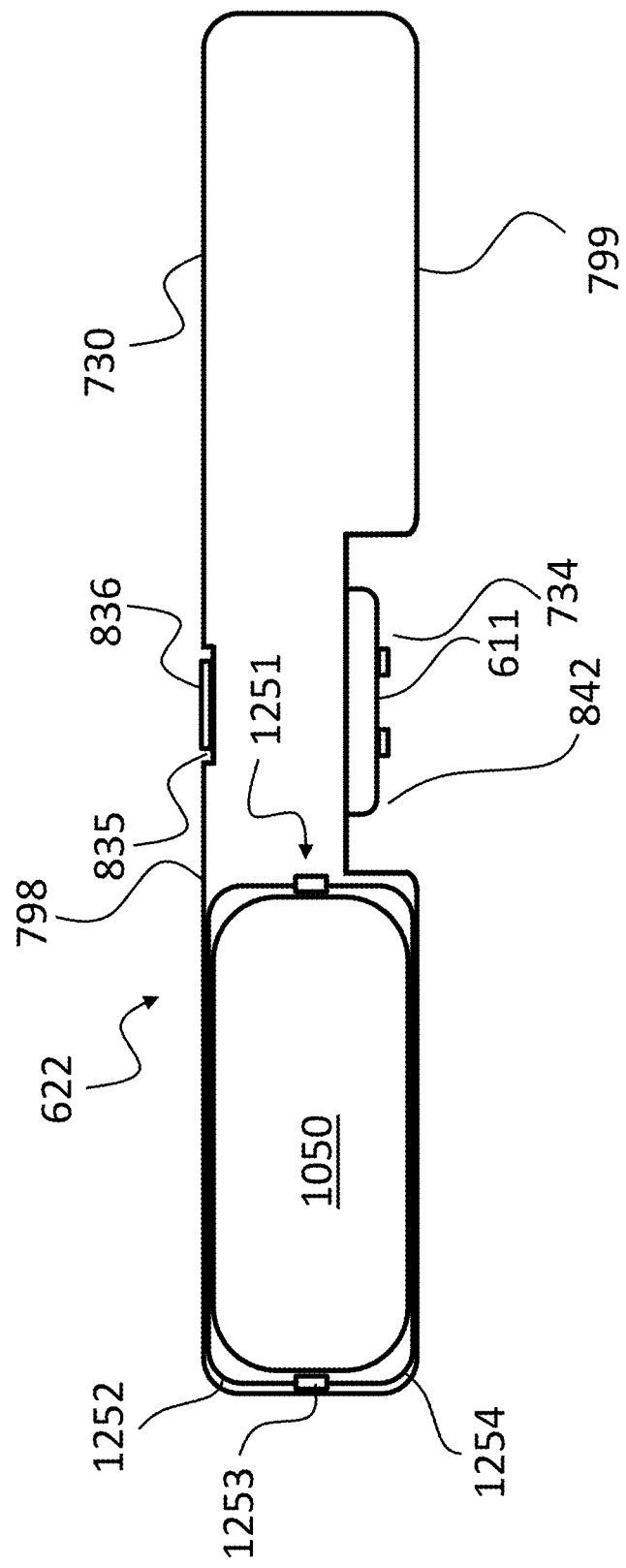

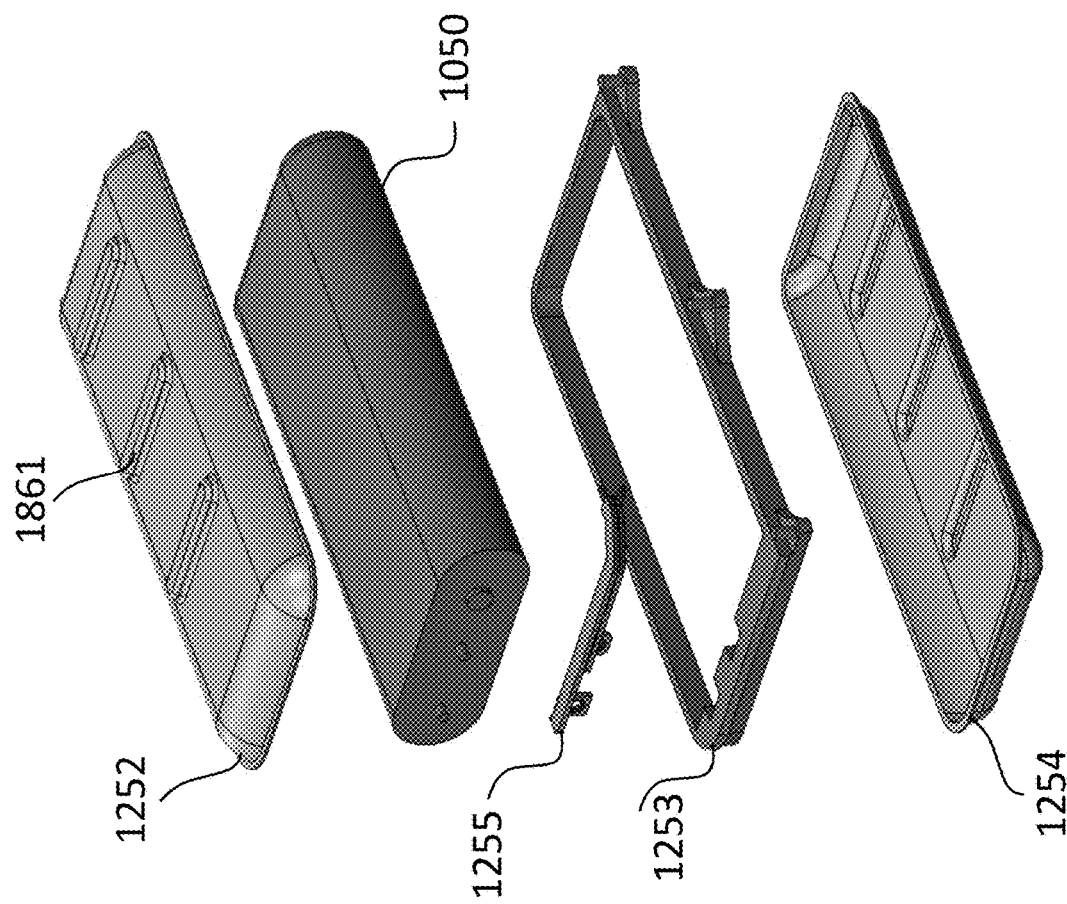

FEEDTHROUGH PLACEMENT

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound. Other types of hearing prostheses include without limitation bone conduction devices and middle ear implants.

SUMMARY

An exemplary embodiment includes a device, comprising a housing of a medical device configured to be implanted in a human recipient, the housing having at least one opening on one side of the housing; and a linear feedthrough assembly, wherein the linear feedthrough assembly closes the opening to form part of a hermetic enclosure of the device, the housing has a length, a width, and a height, wherein the height is the smallest dimension, and the opening is located in at least about the center of at least one of the length or the width, and the opening faces a direction normal to a plane established by the length and the width.

An exemplary embodiment also includes an implantable housing of a hearing prosthesis, the housing having an opening; a battery located in the housing; an electronics assembly located in the housing; and a feedthrough, wherein the feedthrough closes the opening, establishing a portion of a hermetically sealed enclosure of the device, the device includes a plurality of feedthrough conductors, wherein the conductors are arranged in a linear manner, and the feedthrough includes a conductor that is included in the plurality of feedthrough conductors arranged in a linear manner.

In another exemplary embodiment, there is a device, comprising: a housing of a hearing prosthesis, the housing having an opening; a battery located in the housing; and a feedthrough assembly located in the opening, wherein the housing has a length, a width, and a height, the height being the smallest dimension, wherein with respect to an axis normal to the length and the width, a plane normal to the axis extends through at least a portion of the feedthrough assembly and through at least a portion of the battery, the device is hermetically sealed, and the feedthrough assembly establishes a portion of the hermetic seal.

In another exemplary embodiment, there is a device, comprising: an implantable housing of a hearing prosthesis, the housing having an opening; a battery assembly located in the housing; and a feedthrough assembly, the feedthrough assembly extending through a housing wall of the housing, wherein the battery assembly provides structural reinforcement to the housing, and the area at and around the feedthrough assembly is hermetically sealed.

BRIEF DESCRIPTION OF THE DRAWINGS

Embodiments are described below with reference to the attached drawings, in which:

FIG. 1C is a side view of an exemplary hearing prosthesis in which at least some of the teachings detailed herein are applicable;

FIG. 2A is a functional block diagram of a prosthesis, in accordance with embodiments of the present invention;

FIG. 3A is a functional block diagram of a cochlear implant, in accordance with embodiments of the present invention;

FIG. 3C is yet another alternate functional block diagram of a cochlear implant, in accordance with embodiments of the present invention;

FIG. 4A is a simplified schematic diagram of a transceiver unit of an external device in accordance with embodiments of the present invention;

FIG. 4B is a simplified schematic diagram of a transmitter unit of an external device in accordance with embodiments of the present invention;

FIG. 4C is a simplified schematic diagram of a stimulator/receiver unit including a data receiver of an implantable device in accordance with embodiments of the present invention;

FIG. 4D is a simplified schematic diagram of a stimulator/receiver unit including a data transceiver of an implantable device in accordance with embodiments of the present invention;

FIG. 4E is a simplified schematic diagram of a stimulator/receiver unit including a data receiver and a communication component configured to vary the effective coil area of an implantable device in accordance with embodiments of the present invention;

FIG. 4F is a simplified schematic diagram of a stimulator/receiver unit including a data transceiver and a communication component configured to vary the effective coil area of an implantable device in accordance with embodiments of the present invention;

FIG. 5 is a schematic of an exemplary implantable component utilizing feedthroughs;

FIG. 6 is a schematic of another exemplary implantable component utilizing feedthroughs;

FIG. 7 is a bottom view of an exemplary stimulator unit according to an exemplary embodiment;

FIG. 8 is a side view of the stimulator unit of FIG. 7;

FIGS. 14-15B provide additional details according to some exemplary embodiments; and FIGS. 16-18 provide details associated with the battery of the stimulator unit according to some embodiments.

DETAILED DESCRIPTION

Exemplary embodiments will be described in terms of a cochlear implant. That said, it is noted that the teachings detailed herein and/or variations thereof can be utilized with other types of hearing prostheses, such as by way of example, bone conduction devices, DACI/DACS/middle ear implants, etc. Still further, it is noted that the teachings detailed herein and/or variations thereof can be utilized with other types of prostheses, such as pacemakers, muscle stimulators, etc. In some instances, the teachings detailed herein and/or variations thereof are applicable to any type of implanted component that utilizes feedthroughs.

Figure 1A:
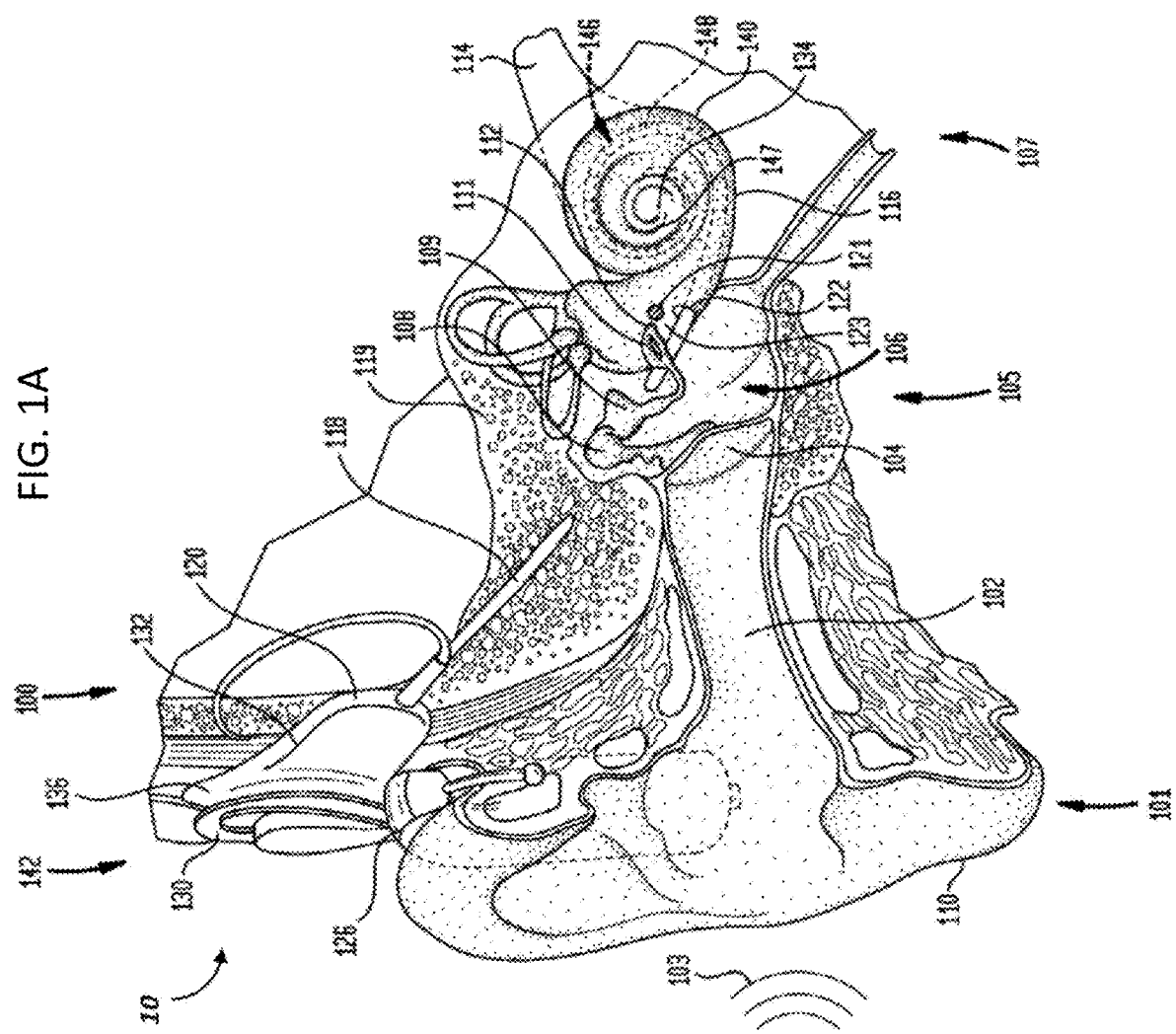
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prostheses, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, and where the implanted cochlear implant includes a battery, that is recharged by the power provided from the external device 142.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil assembly 137. Internal coil assembly 137 typically includes a wire antenna coil comprised of multiple turns of electrically insulated single-strand or multi-strand platinum or gold wire, as will be described in greater detail below.

Cochlear implant 100 further comprises a main implantable component 120 and an elongate electrode assembly 118. Collectively, the coil assembly 137, the main implantable component 120, and the electrode assembly 118 correspond to the implantable component of the system 10.

In some embodiments, internal energy transfer assembly 132 and main implantable component 120 are hermetically sealed within a biocompatible housing or within the device in general (the housing per se may not be hermetically sealed). In some embodiments, main implantable component 120 includes an implantable microphone assembly (not shown) and a sound processing unit (not shown) to convert the sound signals received by the implantable microphone or via internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown in FIG. 1A) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
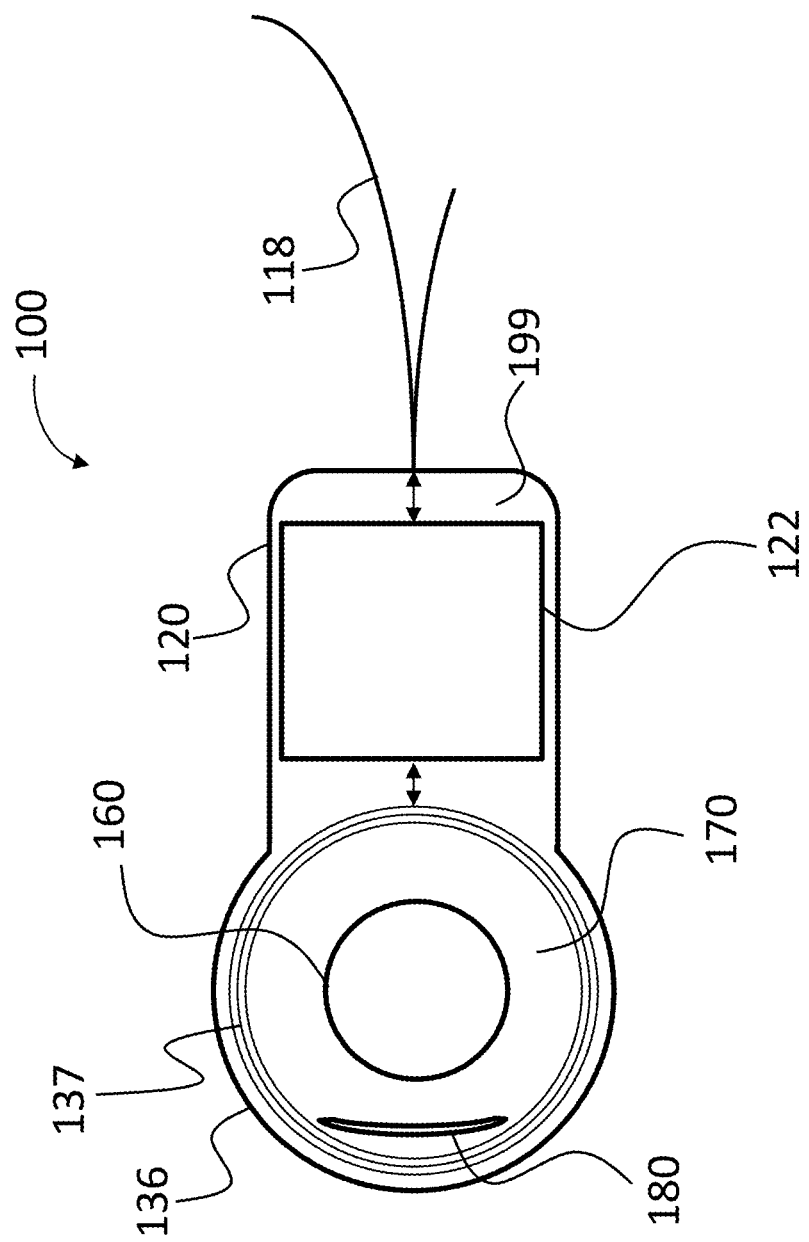
FIG. 1B is a top view of an exemplary hearing prosthesis in which at least some of the teachings detailed herein are applicable.

FIG. 1B depicts an exemplary high-level diagram of the implantable component 100 of the system 10, looking downward from outside the skull towards the skull. As can be seen, implantable component 100 includes a magnet 160 that is surrounded by a coil 137 that is in two-way communication (although in some instances, the communication is one-way) with a stimulator unit 122, which in turn is in communication with the electrode assembly 118.

Still with reference to FIG. 1B, it is noted that the stimulator unit 122, and the magnet apparatus 160 are located in a housing made of an elastomeric material 199, such as by way of example only and not by way of limitation, silicone. Hereinafter, the elastomeric material 199 of the housing will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

As can be seen in FIG. 1B, the housing made of elastomeric material 199 includes a slit 180 (not shown in FIG. 1C, as, in some instances, the slit is not utilized). In some variations, the slit 180 has utilitarian value in that it can enable insertion and/or removal of the magnet apparatus 160 from the housing made of elastomeric material 199.

It is noted that magnet apparatus 160 is presented in a conceptual manner. In this regard, it is noted that in at least some instances, the magnet apparatus 160 is an assembly that includes a magnet surrounded by a biocompatible coating. Still further by way of example, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container. Additional details of the container will be described below. In this regard, it is noted that while sometimes the term magnet is used as shorthand for the phrase magnet apparatus, and thus any disclosure herein with respect to a magnet also corresponds to a disclosure of a magnet apparatus according to the aforementioned embodiments and/or variations thereof and/or any other configuration that can have utilitarian value according to the teachings detailed herein.

Briefly, it is noted that there is utilitarian value with respect to enabling the magnet to revolve within the container or otherwise move. In this regard, in an exemplary embodiment, when the magnet is introduced to an external magnetic field, such as in an MRI machine, the magnet can revolve or otherwise move to substantially align with the external magnetic field. In an exemplary embodiment, this alignment can reduce or otherwise eliminate the torque on the magnet, thus reducing discomfort and/or reducing the likelihood that the implantable component will be moved during the MRI procedure (potentially requiring surgery to place the implantable component at its intended location) and thus reduce and/or eliminate the demagnetization of the magnet.

Element 136 can be considered a housing of the coil, in that it is part of the housing 199.

With reference now to FIG. 1C, it is noted that the outlines of the housing made from elastomeric material 199 are presented in dashed line format for ease of discussion. In an exemplary embodiment, silicone or some other elastomeric material fills the interior within the dashed line, other than the other components of the implantable device (e.g., plates, magnet, stimulator, etc.). That said, in an alternative embodiment, silicone or some other elastomeric material substantially fills the interior within the dashed lines other than the components of the implantable device (e.g., there can be pockets within the dashed line in which no components and no silicone are located).

It is noted that FIGS. 1B and 1C are conceptual FIGs. presented for purposes of discussion. Commercial embodiments corresponding to these FIGs. can be different from that depicted in the figures.

FIG. 2A is a functional block diagram of a prosthesis 200A in accordance with embodiments of the present invention. Prosthesis 200A comprises an implantable component 244 configured to be implanted beneath a recipient's skin or other tissue 250 and an external device 204. For example, implantable component 244 may be implantable component 100 of FIG. 1A, and external device may be the external device 142 of FIG. 1A. Similar to the embodiments described above with reference to FIG. 1A, implantable component 244 comprises a transceiver unit 208 which receives data and power from external device 204. External device 204 transmits power and data 220 via transceiver unit 206 to transceiver unit 208 via a magnetic induction data link 220. As used herein, the term receiver refers to any device or component configured to receive power and/or data such as the receiving portion of a transceiver or a separate component for receiving. The details of transmission of power and data to transceiver unit 208 are provided below. With regard to transceivers, it is noted at this time that while embodiments of the present invention may utilize transceivers, separate receivers and/or transmitters may be utilized as appropriate. This will be apparent in view of the description below.

Implantable component 244 may comprises a power storage element 212 and a functional component 214. Power storage element 212 is configured to store power received by transceiver unit 208, and to distribute power, as needed, to the elements of implantable component 244. Power storage element 212 may comprise, for example, a rechargeable battery 212. An example of a functional component may be a stimulator unit 120 as shown in FIG. 1B.

In certain embodiments, implantable component 244 may comprise a single unit having all components of the implantable component 244 disposed in a common housing. In other embodiments, implantable component 244 comprises a combination of several separate units communicating via wire or wireless connections. For example, power storage element 212 may be a separate unit enclosed in a hermetically sealed device, such as the housing, or the combination of the housing and other components, etc. The implantable magnet apparatus and plates associated therewith may be attached to or otherwise be a part of any of these units, and more than one of these units can include the magnet apparatus and plates according to the teachings detailed herein and/or variations thereof.

In the embodiment depicted in FIG. 2A, external device 204 includes a data processor 210 that receives data from data input unit 211 and processes the received data. The processed data from data processor 210 is transmitted by transceiver unit 206 to transceiver unit 208. In an exemplary embodiment, data processor 210 may be a sound processor, such as the sound processor of FIG. 1A for the cochlear implant thereof, and data input unit 211 may be a microphone of the external device.

Figure 2B:
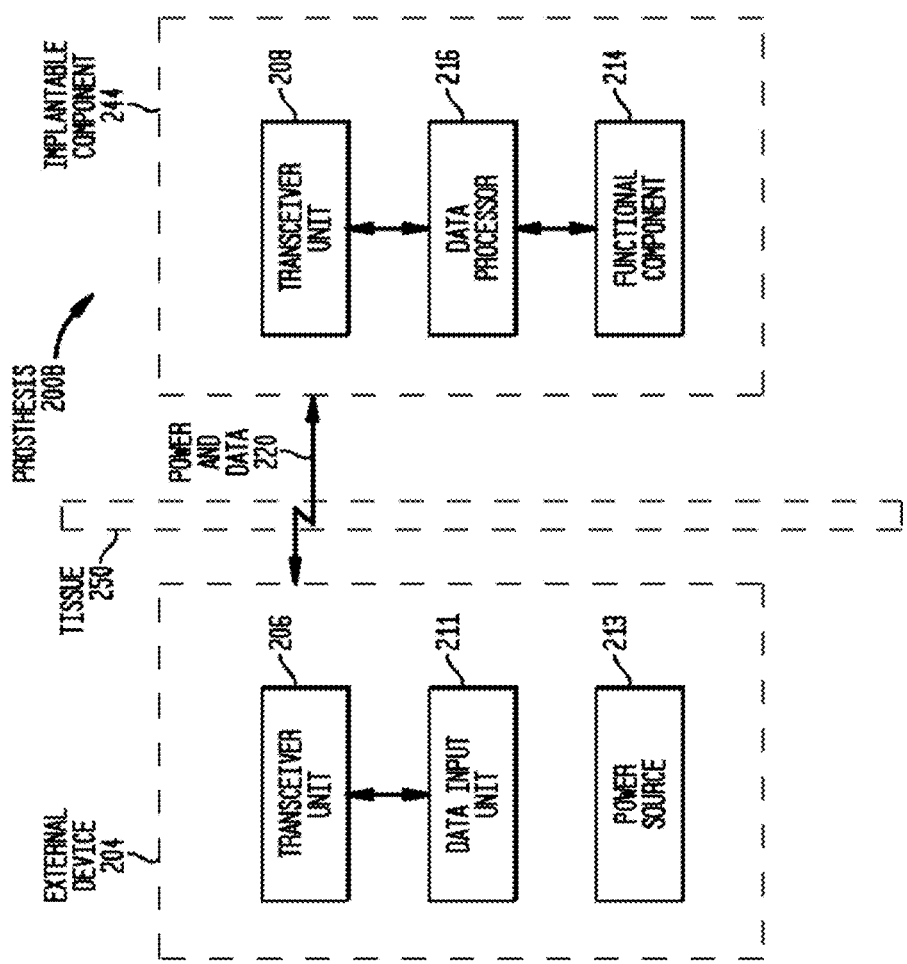
FIG. 2B is an alternate functional block diagram of a prosthesis, in accordance with embodiments of the present invention.

FIG. 2B presents an alternate embodiment of the prosthesis 200A of FIG. 2A, identified in FIG. 2B as prosthesis 200B. As may be seen from comparing FIG. 2A to FIG. 2B, the data processor can be located in the external device 204 or can be located in the implantable component 244. In some embodiments, both the external device 204 and the implantable component 244 can include a data processor.

As shown in FIGS. 2A and 2B, external device 204 can include a power source 213. Power from power source 213 can be transmitted by transceiver unit 206 to transceiver unit 208 to provide power to the implantable component 244, as will be described in more detail below.

While not shown in FIGS. 2A and 2B, external device 204 and/or implantable component 244 include respective inductive communication components. These inductive communication components can be connected to transceiver unit 206 and transceiver unit 208, permitting power and data 220 to be transferred between the two units via magnetic induction.

As used herein, an inductive communication component includes both standard induction coils and inductive communication components configured to vary their effective coil areas.

As noted above, prosthesis 200A of FIG. 2A may be a cochlear implant. In this regard, FIG. 3A provides additional details of an embodiment of FIG. 2A where prosthesis 200A is a cochlear implant. Specifically, FIG. 3A is a functional block diagram of a cochlear implant 300 in accordance with embodiments of the present invention.

It is noted that the components detailed in FIGS. 2A and 2B may be identical to the components detailed in FIG. 3A, and the components of 3A may be used in the embodiments depicted in FIGS. 2A and 2B.

Cochlear implant 300A comprises an implantable component 344A (e.g., implantable component 100 of FIG. 1) configured to be implanted beneath a recipient's skin or other tissue 250, and an external device 304A. External device 304A may be an external component such as external component 142 of FIG. 1.

Similar to the embodiments described above with reference to FIGS. 2A and 2B, implantable component 344A comprises a transceiver unit 208 (which may be the same transceiver unit used in FIGS. 2A and 2B) which receives data and power from external device 304A. External device 304A transmits data and/or power 320 to transceiver unit 208 via a magnetic induction data link. This can be done while charging module 212.

Implantable component 344A also comprises a power storage element 212, electronics module 322 (which may include components such as sound processor 126 and/or may include a stimulator unit 332 corresponding to stimulator unit 122 of FIG. 1B) and an electrode assembly 348 (which may include an array of electrode contacts 148 of FIG. 1A). Power storage element 212 is configured to store power received by transceiver unit 208, and to distribute power, as needed, to the elements of implantable component 344A.

As shown, electronics module 322 includes a stimulator unit 332. Electronics module 322 can also include one or more other functional components used to generate or control delivery of electrical stimulation signals 315 to the recipient. As described above with respect to FIG. 1A, electrode assembly 348 is inserted into the recipient's cochlea and is configured to deliver electrical stimulation signals 315 generated by stimulator unit 332 to the cochlea.

In the embodiment depicted in FIG. 3A, the external device 304A includes a sound processor 310 configured to convert sound signals received from sound input unit 311 (e.g., a microphone, an electrical input for an FM hearing system, etc.) into data signals. In an exemplary embodiment, the sound processor 310 corresponds to data processor 210 of FIG. 2A.

Figure 3B:
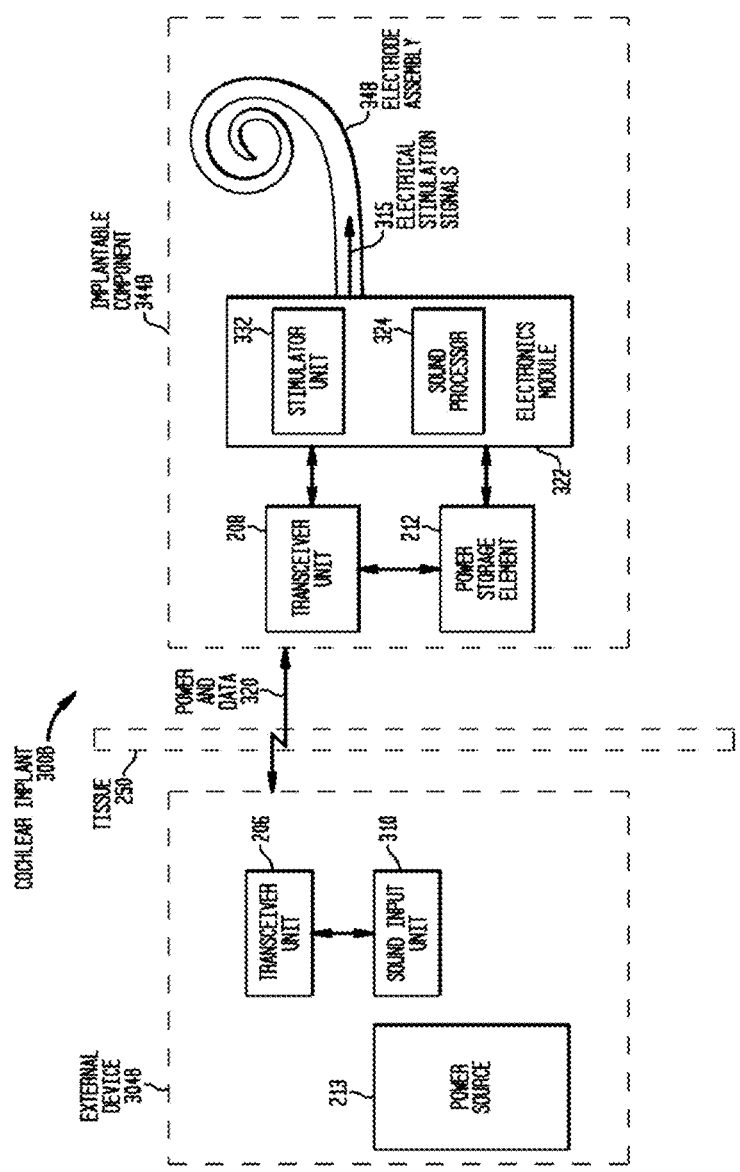
FIG. 3B is an alternate functional block diagram of a cochlear implant, in accordance with embodiments of the present invention.

FIG. 3B presents an alternate embodiment of a cochlear implant 300B. The elements of cochlear implant 300B correspond to the elements of cochlear implant 300A, except that external device 304B does not include sound processor 310. Instead, the implantable component 344B includes a sound processor 324, which may correspond to sound processor 310 of FIG. 3A.

As will be described in more detail below, while not shown in the figures, external device 304A/304B and/or implantable component 344A/344B include respective inductive communication components.

FIGS. 3A and 3B illustrate that external device 304A/304B can include a power source 213, which may be the same as power source 213 depicted in FIG. 2A. Power from power source 213 can be transmitted by transceiver unit 306 to transceiver unit 308 to provide power to the implantable component 344A/344B, as will be detailed below. FIGS. 3A and 3B further detail that the implantable component 344A/344B can include a power storage element 212 that stores power received by the implantable component 344 from power source 213. Power storage element 212 may be the same as power storage element 212 of FIG. 2A.

In contrast to the embodiments of FIGS. 3A and 3B, as depicted in FIG. 3C, an embodiment of the present invention of a cochlear implant 300C includes an implantable component 344C that does not include a power storage element 212. In the embodiment of FIG. 3C, sufficient power is supplied by external device 304A/304B in real time to power implantable component 344C without storing power in a power storage element. In FIG. 3C, all of the elements are the same as FIG. 3A except for the absence of power storage element 212.

Some of the components of FIGS. 3A-3C will now be described in greater detail.

FIG. 4A is a simplified schematic diagram of a transceiver unit 406A in accordance with an embodiment of the present invention. An exemplary transceiver unit 406A may correspond to transceiver unit 206 of FIGS. 2A-3C. As shown, transceiver unit 406A includes a power transmitter 412 *a*, a data transceiver 414A and an inductive communication component 416.

In an exemplary embodiment, as will be described in more detail below, inductive communication component 416 comprises one or more wire antenna coils (depending on the embodiment) comprised of multiple turns of electrically insulated single-strand or multi-strand platinum or gold wire (thus corresponding to coil 137 of FIG. 1B). Power transmitter 412A comprises circuit components that inductively transmit power from a power source, such as power source 213, via an inductive communication component 416 to implantable component 344A/B/C (FIGS. 3A-3C). Data transceiver 414A comprises circuit components that cooperate to output data for transmission to implantable component 344A/B/C (FIGS. 3A-3C). Transceiver unit 406A can receive inductively transmitted data from one or more other components of cochlear implant 300A/B/C, such as telemetry or the like from implantable component 344A (FIG. 3A).

Transceiver unit 406A can be included in a device that includes any number of components which transmit data to implantable component 334A/B/C. For example, the transceiver unit 406A may be included in a behind-the-ear (BTE) device having one or more of a microphone or sound processor therein, an in-the-ear device, etc.

FIG. 4B depicts a transmitter unit 406B, which is identical to transceiver unit 406A, except that it includes a power transmitter 412B and a data transmitter 414B.

It is noted that for ease of description, power transmitter 412A and data transceiver 414A/data transmitter 414B are shown separate. However, it should be appreciated that in certain embodiments, at least some of the components of the two devices may be combined into a single device.

FIG. 4C is a simplified schematic diagram of one embodiment of an implantable component 444A that corresponds to implantable component 344A of FIG. 3A, except that transceiver unit 208 is a receiver unit. In this regard, implantable component 444A comprises a receiver unit 408A, a power storage element, shown as rechargeable battery 446, and electronics module 322, corresponding to electronics module 322 of FIG. 3A. Receiver unit 408A includes an inductance coil 442 connected to receiver 441. Receiver 441 comprises circuit components which receive, via an inductive communication component corresponding to an inductance coil 442, inductively transmitted data and power from other components of cochlear implant 300A/B/C, such as from external device 304A/B. The components for receiving data and power are shown in FIG. 4C as data receiver 447 and power receiver 449. For ease of description, data receiver 447 and power receiver 449 are shown separate. However, it should be appreciated that in certain embodiments, at least some of the components of these receivers may be combined into one component.

In the illustrative embodiments of the present invention, receiver unit 408A and transceiver unit 406A (or transmitter unit 406B) establish a transcutaneous communication link over which data and power is transferred from transceiver unit 406A (or transmitter unit 406B), to implantable component 444A. As shown, the transcutaneous communication link comprises a magnetic induction link formed by an inductance communication component system that includes inductive communication component 416 and coil 442.

The transcutaneous communication link established by receiver unit 408A and transceiver unit 406A (or whatever other viable component can so establish such a link), in an exemplary embodiment, may use time interleaving of power and data on a single radio frequency (RF) channel or band to transmit the power and data to implantable component 444A. A method of time interleaving power according to an exemplary embodiment uses successive time frames, each having a time length and each divided into two or more time slots. Within each frame, one or more time slots are allocated to power, while one or more time slots are allocated to data. In an exemplary embodiment, the data modulates the RF carrier or signal containing power. In an exemplary embodiment, transceiver unit 406A and transmitter unit 406B are configured to transmit data and power, respectively, to an implantable component, such as implantable component 344A, within their allocated time slots within each frame.

The power received by receiver unit 408A can be provided to rechargeable battery 446 for storage. The power received by receiver unit 408A can also be provided for distribution, as desired, to elements of implantable component 444A. As shown, electronics module 322 includes stimulator unit 332, which in an exemplary embodiment corresponds to stimulator unit 322 of FIGS. 3A-3C, and can also include one or more other functional components used to generate or control delivery of electrical stimulation signals to the recipient.

In an embodiment, implantable component 444A comprises a receiver unit 408A, rechargeable battery 446 and electronics module 322 integrated in a single implantable housing, referred to as stimulator/receiver unit 406A. It would be appreciated that in alternative embodiments, implantable component 344 may comprise a combination of several separate units communicating via wire or wireless connections.

FIG. 4D is a simplified schematic diagram of an alternate embodiment of an implantable component 444B. Implantable component 444B is identical to implantable component 444A of FIG. 4C, except that instead of receiver unit 408A, it includes transceiver unit 408B. Transceiver unit 408B includes transceiver 445 (as opposed to receiver 441 in FIG. 4C). Transceiver unit 445 includes data transceiver 451 (as opposed to data receiver 447 in FIG. 4C).

FIGS. 4E and 4F depict alternate embodiments of the implantable components 444A and 444B depicted in FIGS. 4C and 4D, respectively. In FIGS. 4E and 4F, instead of coil 442, implantable components 444C and 444D (FIGS. 4E and 4F, respectively) include inductive communication component 443. Inductive communication component 443 is configured to vary the effective coil area of the component, and may be used in cochlear implants where the exterior device 304A/B does not include a communication component configured to vary the effective coil area (i.e., the exterior device utilizes a standard inductance coil). In other respects, the implantable components 444C and 444D are substantially the same as implantable components 444A and 444B. Note that in the embodiments depicted in FIGS. 4E and 4F, the implantable components 444C and 444D are depicted as including a sound processor 342. In other embodiments, the implantable components 444C and 444D may not include a sound processor 342.

FIG. 5 depicts an exemplary alternate embodiment of an implantable component of a cochlear implant in a modularized form. Here, implantable component 500 corresponds to the implantable component 100 detailed above with respect to functionality and componentry, except that the electrode assembly is readily removable from the stimulator unit and the implantable coil is also readily removable from the stimulator unit (as opposed to the stimulator unit and the implantable coil being held together by the housing made of elastomeric material 199 as detailed above, and the elongate electrode assembly 118 being effectively permanently attached to the stimulator unit). More particularly, the implantable component 500 includes a stimulator unit 522 that includes one or more feedthrough assemblies that permit removable attachment of the coil and the electrode array to the stimulator unit 522. In this regard, as can be seen, the implantable component 500 includes a coil unit 537 that includes a coil 517 located in a silicone body 538, and an electrical lead assembly 512 with a connector that is connected to a feedthrough 513 of the stimulator unit 522, thus placing the coil 517 into signal communication with the electronic assembly of the stimulator unit 522. On the opposite size of the stimulator unit 522 is feedthrough 511 of the stimulator unit 522. Attached to the feedthrough 511 is the electrode assembly 518, which includes lead 519 to which is attached to electrode array at the distal end thereof, and includes connector 510 that is attached to feedthrough 511, thus placing the electrode array into signal communication with the stimulator unit 522. In an exemplary embodiment, the connectors 510 and 512 are removable from the feedthroughs 511 and 513, respectively, thus enabling the electrode assembly 518 and the coil unit 537 to be removed from signal communication with the stimulator unit 522. Such can have utilitarian value with respect to a scenario where the stimulator unit 522 and/or the coil unit 537 has need of replacement, and thus those components can be removed from the recipient without removing the electrode assembly 518 in general, and the electrode array thereof, in particular, from the recipient.

FIG. 6 depicts another exemplary alternate embodiment of an implantable component of a cochlear implant in a modularized form. As with implantable component 500, implantable component 600 corresponds to the implantable component 100 detailed above with respect to functionality and componentry, except that the electrode assembly is readily removable from the stimulator unit and the implantable coil is also readily removable from the stimulator unit (as opposed to the stimulator unit and the implantable coil being held together by the housing made of elastomeric material 199 as detailed above, and the elongate electrode assembly 118 being effectively permanently attached to the stimulator unit). More particularly, the implantable component 600 includes a stimulator unit 622 that includes one or more feedthrough assemblies that permit removable attachment of the coil and the electrode array to the stimulator unit 522. In this regard, as can be seen, the implantable component 600 includes a coil unit 637 that includes a coil 517 located in a silicone body, and an electrical lead assembly 612 with a connector that is connected to a feedthrough 613 of the stimulator unit 622, thus placing the coil 617 into signal communication with the electronic assembly of the stimulator unit 622. As can be seen, instead of the feedthrough 613 being on the side of the stimulator unit 622, it is on the bottom (the skull-facing side). Also, a feedthrough 611 of the stimulator unit 522 is located adjacent feedthrough 613 on the bottom of the unit 622. Attached to the feedthrough 611 is the electrode assembly 618, which includes a lead to which is attached to electrode array at the distal end thereof, and includes connector 610 that is attached to feedthrough 611, thus placing the electrode array into signal communication with the stimulator unit 522. In an exemplary embodiment, the connectors 610 and 612 are removable from the feedthroughs 611 and 613, respectively, thus enabling the electrode assembly 618 and the coil unit 637 to be removed from signal communication with the stimulator unit 622. In this embodiment, movement of the connectors downward, away from the stimulator unit 622 detaches the connectors from the respective feedthroughs. As with the embodiment of FIG. 5, such can have utilitarian value with respect to a scenario where the stimulator unit 622 and/or the coil unit 637 has need of replacement, and thus those components can be removed from the recipient without removing the electrode assembly 618 in general, and the electrode array thereof in particular, from the recipient.

Some utilitarian features of having the feedthroughs at the bottom of the stimulator unit will be described below. However, some additional features of some exemplary embodiments of the stimulator unit 622 will now be described.

FIG. 7 depicts a bottom view of the stimulator unit 622 without connectors 610 and 612 attached thereto. As can be seen, the feedthroughs 611 and 613 can be seen. Note that with respect to an implanted stimulator unit 622, this view is looking upwards from the skull. That is, the surface 799 is the surface that contacts the skull (although it is noted that in some embodiments, the features herein with regard to the bottom are instead or in addition to this applied to the top—e.g., FIG. 7 can depict the top/FIG. 7 can depict both the top and the bottom). Stimulator 622 includes a housing 730 which supports the feedthroughs 611 and 613. Depicted are electrical contacts 720 extending out the bottom of the feedthroughs 611 and 613. As can be seen, the feedthrough conductors have varying cross-sectional sizes. Two different cross-sectional sizes are depicted in FIG. 7. In this embodiment, the feedthroughs 611 and 613 are aligned along a central axis of the stimulator unit 622/housing 730. Further, the bottoms of the feedthroughs are recessed relative to the bottom surface 799. In this regard, a channel 734 extends from one side of the housing 730 to the other side of the housing, where the local housing wall is elevated (with respect to surface 799 being the bottom) above surface 799. This is more clearly seen in FIG. 8, which depicts a side view of stimulator unit 622. As can be seen, a top surface 798 is parallel to the bottom surface 799, although in other embodiments, the top of the housing 730 may not be parallel to the bottom surface 799 (the top could be a dome-shaped component).

It is noted that connector means any component for attaching the components outside the housing (e.g., the electrode array, the coil, or any other pertinent component), to the housing and establishing a signal communication therebetween. Connector does not require removability. In this regard, a system in which the connections continued uninterrupted through the feedthrough direct to the coil or electrode can be utilized in some embodiments. A removable connector would be removable. In this regard, while the embodiment of FIGS. 6 and 7 are depicted as a modularized system with removable components from the housing, as will be described in greater detail below, embodiments that utilize the teachings detailed herein can include a single component that is generally not separable (at least not without destroying the components), such as that of FIG. 12 described below), where the connectors are permanently attached to the feedthroughs. Indeed, in an exemplary embodiment, the feedthrough is an integral component of the lead assembly, or visa-versa.

The channel 734 is established by sidewalls 842 that extend upwards away from the bottom surface 799. The channel provides a clearance for the feedthrough 611 (and feedthrough 613, which is eclipsed by feedthrough 611 in the view of FIG. 8), and also provides clearance for the connectors of the electrode assembly 618 and the coil unit 637 (or any other connector of any other component that might be connected to the unit 622). In this regard, the stimulator unit 622 and the connectors are configured such that the bottom of the connectors attached to the stimulator unit 622 are above the bottom surface 799, and thus the stimulator unit 622 is supported on bone by surface 799 (as opposed to the connectors). The leads of the connectors extend out the ends of the channel 734 to the respective components. While the embodiment of FIG. 6 depicts the lead for the coil unit extending out one side of the channel and the lead for the electrode assembly extending out another side of the channel, in an alternate embodiment, both leads can extend out the same side of the channel. Note further while the embodiment of FIG. 6 has been depicted as having only two components attached to the stimulator unit 622, in an alternate embodiment, three or more separate components can be attached to the stimulator unit (e.g., in addition to the components of FIG. 6, and implantable microphone can be attached to the stimulator unit, etc.). Still further, in some embodiments, only one component is attached to the stimulator unit. Any arrangement of components can be utilized in at least some embodiments.

Figure 9:
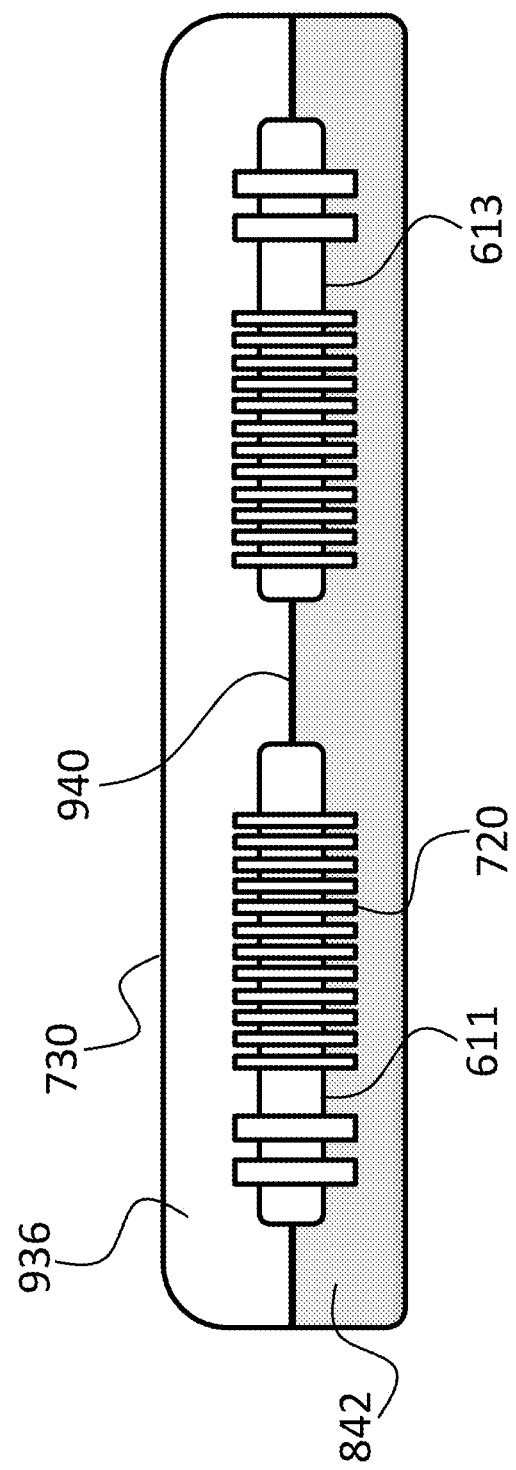
FIG. 9 is a cross-sectional view of the stimulator unit of FIG. 7.

FIG. 9 depicts a cross-sectional view of the stimulator unit 622 relative to FIG. 7. The housing 730 is depicted cut in half, with housing wall 940 (through which the view of FIG. 9 is cut) forming the top of the channel 734, and housing wall 842 in the background behind the feedthroughs 611 and 613. The feedthroughs 611 and 613 extend through housing wall 940, and the electrical contacts 720 extend from the channel 734 to inside the housing 730 (identified as area 936).

Figure 10:
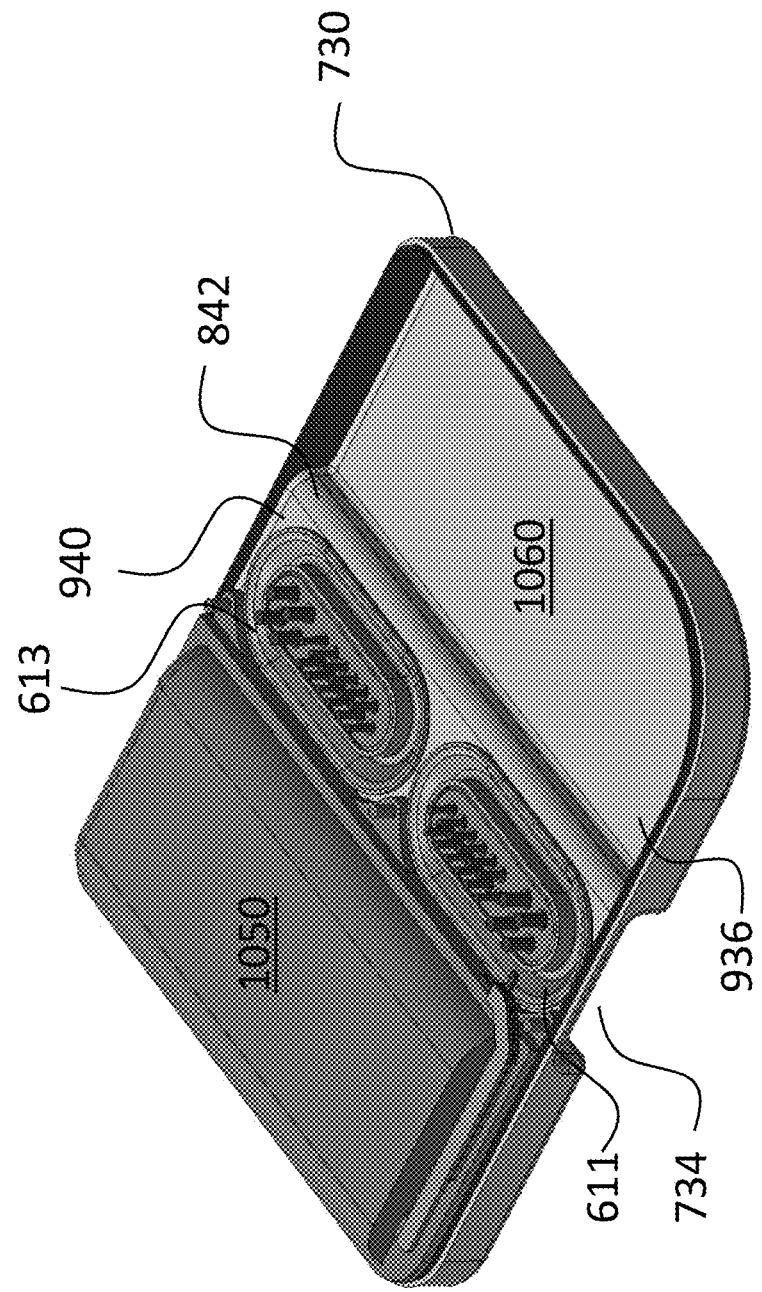
FIG. 10 is a perspective view of a portion of the stimulator unit of FIG. 7.

FIG. 10 depicts an isometric view of a portion of the stimulator unit 622, with the top of the housing 730 removed. As can be seen, feedthroughs 611 and 613 extend through housing wall 940 to the interior of the housing 936. Also depicted is battery 1050 located on one side of the feedthroughs 611 and 613, and an empty space is depicted on the other side of the feedthroughs 611 and 613, where a bottom housing wall 1060, which opposite side establishes the surface 799, can be seen.

In view of the above, in an exemplary embodiment, there is a device, such as a stimulator unit of a cochlear implant, or any other component of an implantable medical device (e.g., a controller for an active transcutaneous bone conduction device, a controller for a pace maker, a controller for a middle ear implant, etc.), comprising a housing (e.g., housing 730) configured to be implanted in a human recipient, the housing having at least one opening on one side of the housing. In the embodiments depicted in FIG. 7, the opening is located on a bone facing side of the housing. That said, in an alternate embodiment, the opening can be located on an opposite side. In this regard, the opening is the opening for one of the feedthroughs 611 or 613. The housing further includes a linear feedthrough assembly (e.g., either of feedthroughs 611 or 613). This as opposed to a non-linear feedthrough assembly (e.g., a circular assembly). In this exemplary embodiment, the linear feedthrough assembly closes the opening. In an exemplary embodiment, the linear feedthrough assembly includes a titanium flange extending about a ceramic body, where electrical contacts extend through the ceramic body, and where the ceramic body electrically isolates the contact from the titanium flange. The titanium flange is welded (e.g. laser welded) to the housing, and thus the linear feedthrough assembly closes the opening. In an exemplary embodiment, the welding results in the establishment of a hermetic seal between the flange and the housing. In some embodiments, each ceramic body has at least 4 electrically isolated paths extending from one side thereof to the other (and thus from inside the housing to the outside of the housing). In some embodiments, each ceramic body has at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more electrically isolated paths extending from one side thereof to the other. With respect to the embodiment of FIG. 7, in an exemplary embodiment, there are at least X (where X can be equal to any of the aforementioned numbers) electrically isolated electrical paths from an outside of the housing to the inside of the housing at the bone facing side of the housing, at least Y of the at least X electrically isolated electrical paths being established by the linear feedthrough assembly. In an exemplary embodiment, Y is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. As will be inferred from this, in an exemplary embodiment, a combination of linear feedthroughs and other types of feedthroughs can be utilized.

Collectively, the device and the feedthroughs, etc., establish a hermetically sealed enclosure.

In an exemplary embodiment, the housing has a length, a width, and a height, wherein the height is the smallest dimension, and the opening is located in at least about the center of at least one of the length or the width, and the opening faces a direction normal to a plane established by the length and the width. This latter feature is seen in FIG. 10. This latter feature is distinguished from the embodiment of FIG. 5, where the opening would face a direction normal to a plane established by the length and the height or the width and the height.

In an exemplary embodiment, the housing is configured to be attached or secured adjacent to bone of the recipient. By way of example only and not by way of limitation, sutures can be utilized to attach the housing to bone. In an alternate embodiment, bone screw fixtures are present. In some embodiments, there is no extra component that is utilized to secure the housing to bone. That said, in an alternate embodiment, the housing is configured to simply lie upon bone or tissue covering a surface of the bone, or be placed elsewhere for that matter. That said, in some alternate embodiments, the housing is configured to be placed away from bone.

In an exemplary embodiment, the at least one opening is a first opening, and the housing includes at least a second opening on the same side of the housing as the first opening (e.g., the bone facing side of the housing). Further, the device includes a second linear feedthrough assembly (e.g., the other of feedthrough 611 or 613), wherein the second linear feedthrough assembly closes the second opening (e.g., just as does the first linear feedthrough). In this exemplary embodiment, consistent with the embodiment of FIG. 7, the first opening and the second opening are located in about one of the center of the length of the width.

In some embodiments, with the first opening and the second opening and respective linear feedthroughs, irrespective of the just noted-features of this embodiment, or in addition thereto, the first opening and the second opening are symmetrically located about the other of the center of the length or the width. In this regard, with respect to the embodiment of FIG. 7, if the horizontal is the length the vertical is the width, the openings are located in the center of the width symmetrically about the length.

Referring back to FIG. 8, an indentation 835 in the top of the housing 730 can be seen. This indentation is for an extra-cochlea electrode (ECE) plate 836. It is noted that in some embodiments, there are two or more indentations for respective ECE plates. In this regard, the aforementioned described device can include a first ECE plate and a second ECE plate located on a side of the housing opposite the side of the housing of the first opening. Here, in this embodiment, the first opening and the second opening and the first ECE plate and the second ECE plate are located in about one of the center of the length or the width. In an exemplary embodiment, the ECE plates are connected by leads to the contacts of one or more of the feedthroughs.

Figure 11:
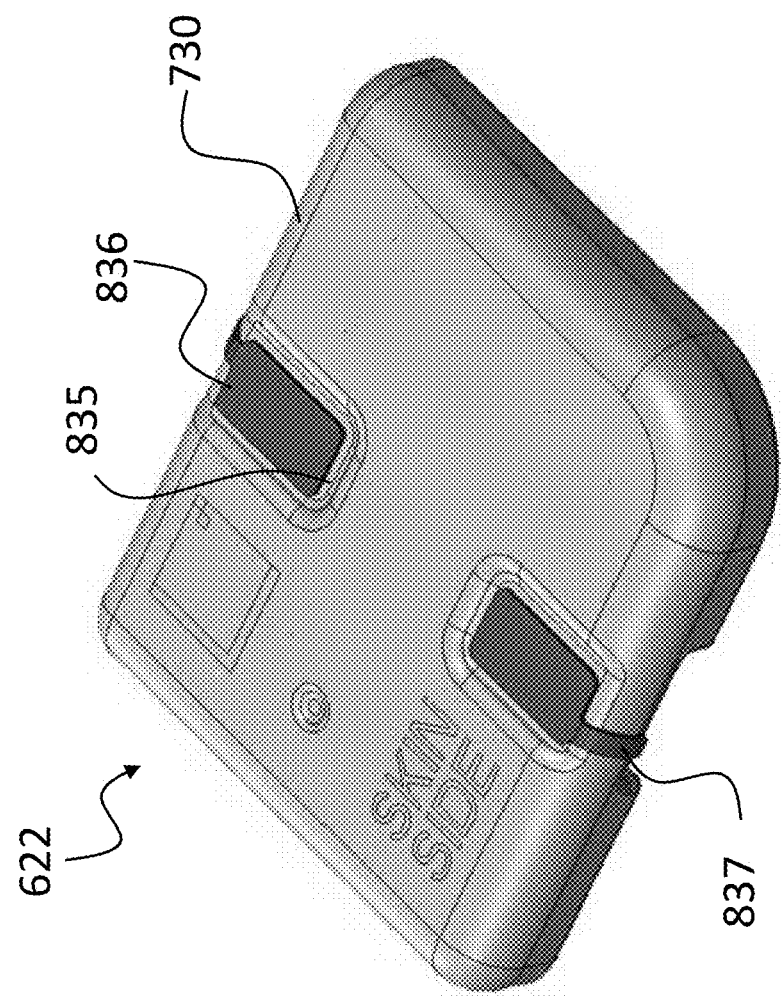
FIG. 11 is a top view of the stimulator unit of FIG. 7.

FIG. 11 depicts an isometric view of the housing 730, and the stimulator unit 622. As can be seen, two ECE plates 836 are located in indentations 835. The indentations and the ECE plates are located in about one of the center of the length or the width of the housing 730, and the ECE plates and the indentations are symmetrically located about the other of the center of the length or the width. As can be seen, conductive components 837 extend from the ECE plate. The conductive components 837 extend to the feedthroughs (and can have a connector configured to interface with the feedthroughs, so as to place the ECE plates into electrical communication with the contacts).

In an exemplary embodiment, with respect to the axis of the housing normal to the length and the width (e.g., in and out of the page of FIG. 7), the first ECE plate is located above the first opening, and the second ECE plate is located above the second opening. In an exemplary embodiment, this alignment facilitates connection of the respective ECE plates to the respective feedthroughs (or the same feedthrough).

It is noted that while the embodiments depicted in FIG. 7 include two separate feedthroughs that are aligned as detailed above, in an exemplary embodiment, only a single feedthrough is utilized. That said, in an alternate embodiment, three or four or five feedthroughs are utilized, again with the alignments detailed above.

With reference to FIGS. 7 and 8 and 9 and 10, in an exemplary embodiment, the bottom of the housing 730 is a complex surface that extends from a first side on a first plane, and then extends on a second plane above the first plane and then extends on a third plane below the second plane. This extension establishes the channel, where the first plane and the third plane are established by respective surfaces 799, and the second plane is established by the wall portion 940. In the embodiment depicted by the figures, the space between the second plane and the first plane provides a clearance between tissue of the recipient upon which the bottom of the unit 622 is supported thereby, and a lead assembly electrically coupled to the feedthrough assembly (any of the lead assemblies of the coil unit 537, the electrode assembly 618, the lead assembly of the ECE plates, etc.).

Figure 12:
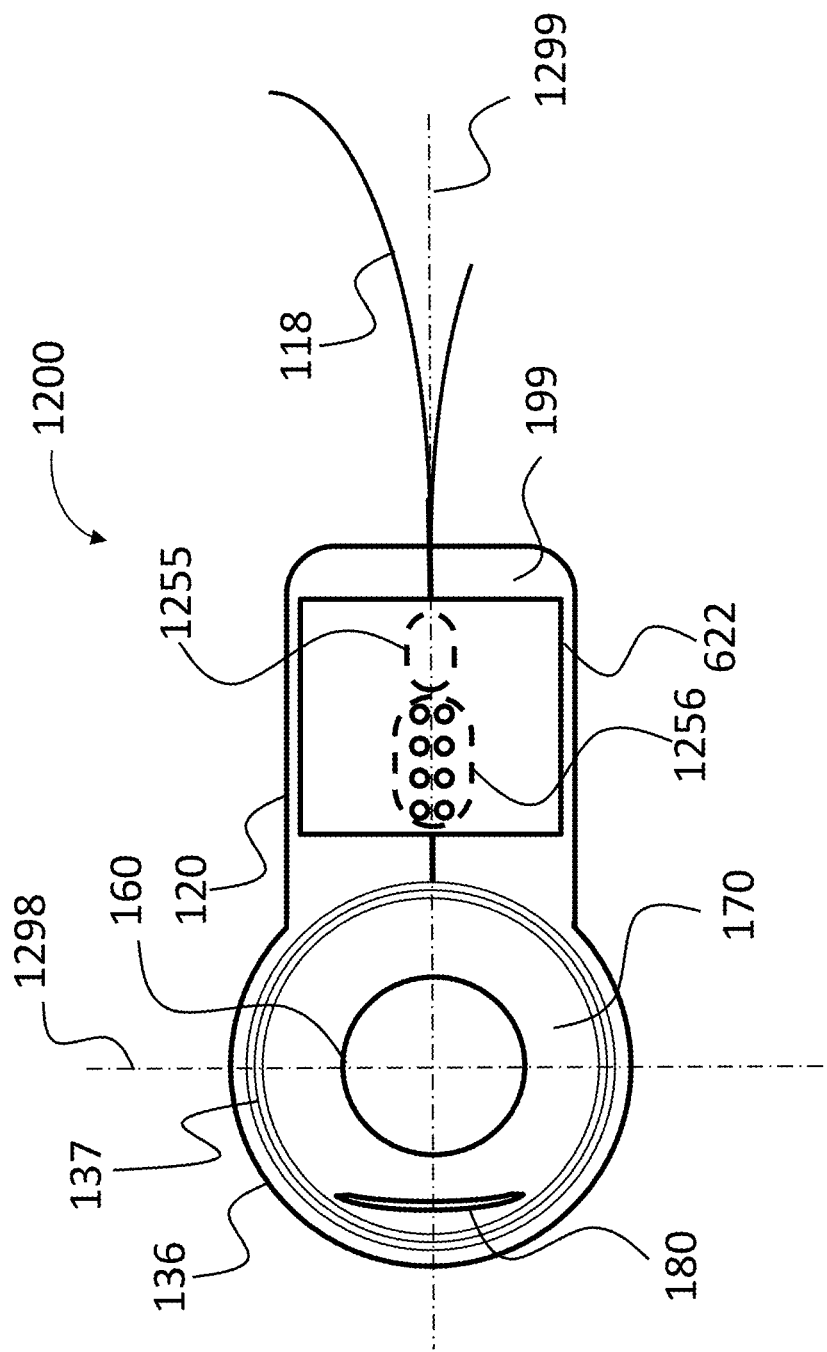
FIG. 12 is a top view of an exemplary implantable component of a cochlear implant according to an exemplary embodiment.

FIG. 12 depicts an exemplary implantable component 1200 of an exemplary embodiment utilizing stimulator unit 622, with the feedthroughs 1256 and 1255 shown in dashed lines (because the feedthroughs are eclipsed by the top of the housing of the stimulator unit 622). In this regard, implantable component 1200 corresponds to implantable component 100 detailed above, where the stimulator unit 622 includes feedthroughs 1256 and 1255 extending out to the bottom of the housing of the stimulator unit 622, consistent with the teachings detailed above. It is noted that in this exemplary embodiment, the feedthroughs 1256 and 1255 are of different designs/geometry, feedthrough 1256 being shorter and wider than feedthrough 1255 (conductors are only shown for feedthrough 1256). Of course, in some embodiments, the same sized/dimension feedthroughs can be utilized. This is but another exemplary embodiment.

In view of FIG. 12, it can be seen that an exemplary embodiment includes an implantable medical device 1200, that includes a housing (the housing of the stimulator unit 622), an induction coil 137, and at least one elongate feedthrough extending through the housing. As can be seen, implantable medical device 1200 includes a longitudinal axis 1299 that extends through a geometric center of the induction coil (the intersection of axis 1299 and line 1298). In this embodiment, the elongate feedthrough is at least generally aligned (including exactly aligned) with the longitudinal axis of the implantable medical device. Still further, as can be seen in FIG. 12, the induction coil 137 is disposed beside a first end of the housing and connected to the elongate feedthrough via the straight lead, and the longitudinal axis 1299 bisects the first end of the housing (at least generally in the center of the housing). Also, with respect to an embodiment such as FIG. 12 where the induction coil 137 is disposed beside a first end of the housing, the implantable medical device 1200 includes an electrical lead that extends from a second end of the housing (the end opposite the end facing the coil 137), and the longitudinal axis 1299 intersects the second end of the housing with respect to the top view thereof at least at the general same location as the electrical lead.

Also, consistent with the features detailed above with respect to the housing 730 having a length, a width, and a height, where the height is the smallest dimension, the housing 730 comprises first and second opposing major faces (e.g., the face facing bone (established by surface 799) and the top, opposite side of the housing) and the elongate feedthrough is recessed in one of the first or second opposing major faces. As noted above, in some embodiments feedthroughs can be recessed in both faces.

Figure 13A:
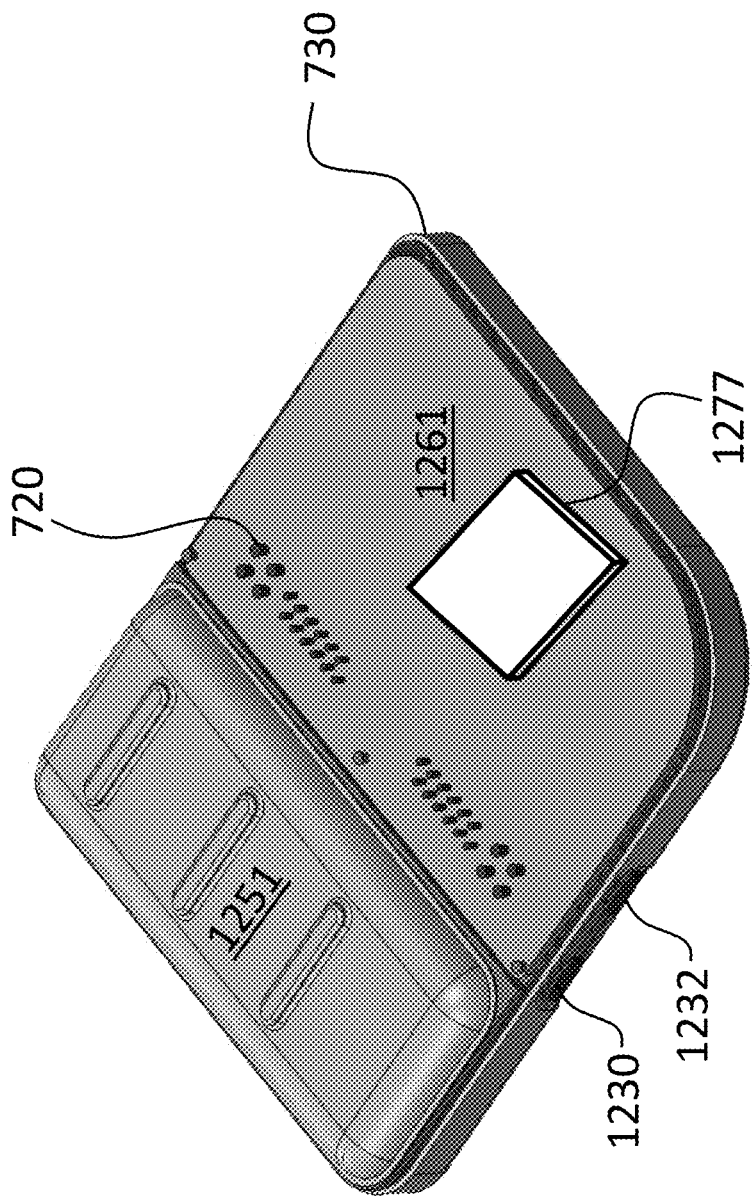
FIG. 13A depicts a portion of the exemplary stimulator unit of FIG. 7.

Still further, FIGS. 7-11 depict an exemplary embodiment of an implantable hermetically sealed device of a hearing prosthesis (e.g., a stimulator unit of a cochlear implant, a control unit of a middle ear implant, etc.), wherein the housing has an opening (the opening through which the feedthrough extends). With reference to FIG. 10, as can be seen, a battery 1050 is located in the housing and a linear feedthrough assembly extends through the housing (either of feedthroughs 611 or 613). The linear feedthrough assemblies close the opening. Also, an electronics assembly is located in the housing. FIG. 13A depicts the electronics assembly 1261 in the housing 730, with contacts 720 of the feedthrough extending through the PCB of the electronics assembly 1261 and in electrical contact with circuitry thereof. Also shown in FIG. 13A is the battery assembly 1251 which includes battery 1050 in an insulated shell. In an exemplary embodiment, the battery is placed in a pressurized shell (as will be discussed in greater detail below).

As with the embodiments detailed above, the housing has a length, a width and a height. With respect to a view looking down on a plane established by the length and the width, the electronics assembly is located on a first side of the housing, the battery is located on a second, opposite side of the housing, and the feedthrough is located between the battery and most of the electronics assembly (where "most" can include all of the electronics assembly). By way of example only and not by way of limitation, if two planes were provided normal to the aforementioned plane established by the length of the width, and a first of these two planes was located between the feedthroughs and the battery assembly 1251, and a second of these two planes was located on an opposite side of the feedthroughs, all of the battery would be located on one side of the first plane, and most of the electronic assembly would be located on an opposite side of the second plane. Consistent with the teachings detailed above, the opening for the feedthrough is located in at least about the center of at least one of the length or the width. Still further, with respect to a view looking down on a plane established by the length and the width, at least one of the battery or the electronics assembly does not overlap the feedthrough, as can be seen.

It is noted that the term "battery" is distinguished from the battery assembly, where the battery assembly includes the casing noted above, and possibly, in some embodiments, connector components that can extend to the feedthroughs or to the electronics components. Here, the term "battery" refers to the cells of the battery that store electricity, and not the components used to conduct the electricity away from those cells.

Still further, it is noted that again with reference to the view looking down on a plane established by the length and the width, at least one of the battery or the electronics assembly does overlap the feedthrough. This is seen in FIG. 13A, where electronics assembly 1261 is shown overlapping the feedthroughs.

In view of the above, in an exemplary embodiment, with respect to a view looking down on a plane established by the length and the width, the battery is located on a first side of the housing, and the feedthrough is located adjacent the battery in a non-overlapping manner.

FIG. 13A depicts a portion of a connector 1230 of an exemplary embodiment. Here, this is a connector portion of the stimulating lead assembly of a cochlear implant (e.g., electrode assembly 618). The rest of the lead assembly has been removed for purposes of clarity. FIG. 13A, in combination with FIG. 6, represents an exemplary embodiment of a cochlear implant, with a lead assembly connected to the feedthrough of the stimulator unit. Consistent with the teachings of FIG. 7, the housing is recessed at the location of the housing that establishes the opening for the feedthrough(s) (the portion establishing the channel 734/the wall portion 940). Thus, FIG. 13A depicts a connector portion 1230 of the stimulating lead assembly located in the recess.

Figure 13B:
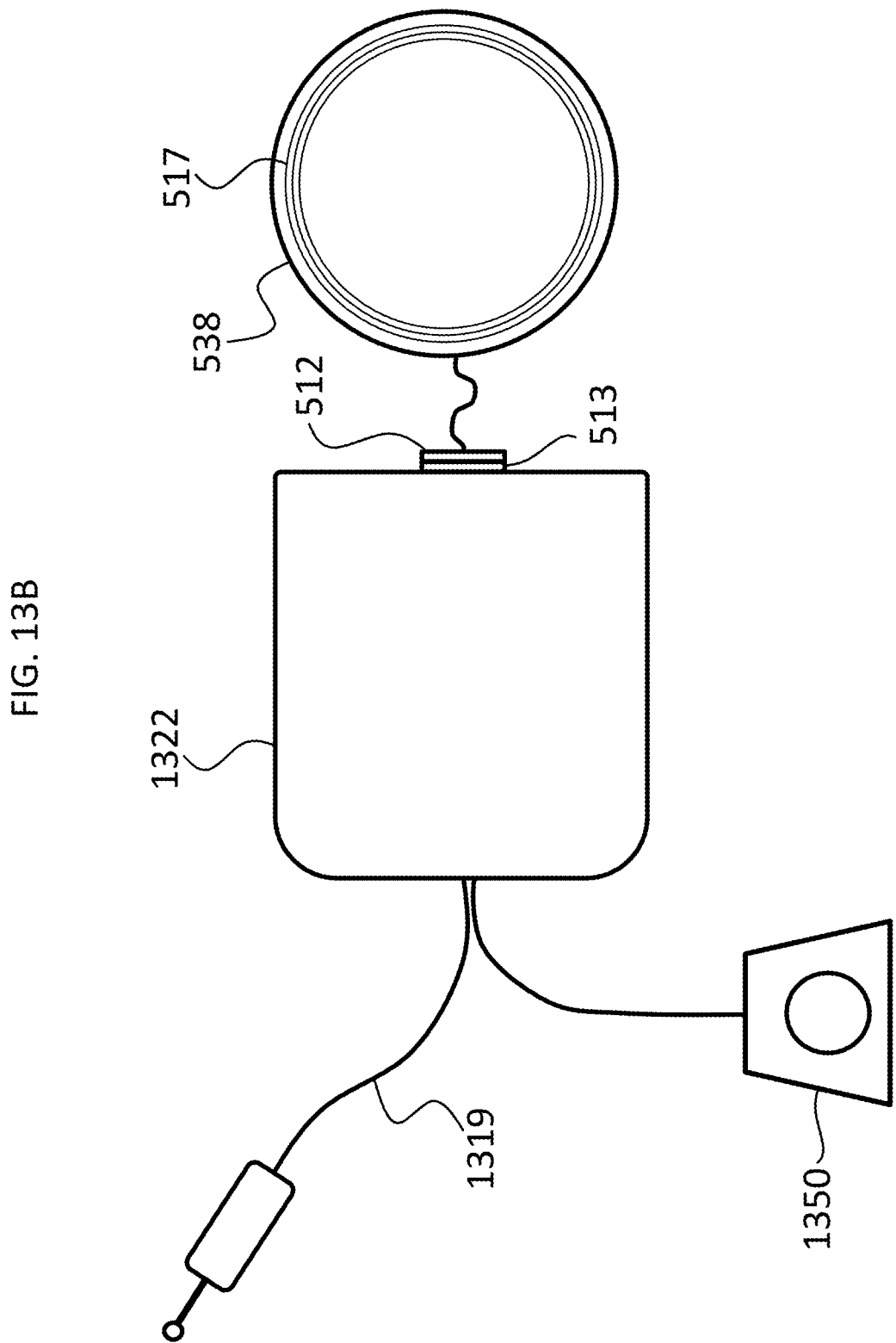
FIG. 13B depicts an exemplary totally implantable hearing prosthesis according to an exemplary embodiment.

FIG. 13A also depicts a second connector, connector 1232, located next to connector 1230 (or, more accurately, FIG. 13A depicts a portion of a connector). Consistent with the teachings detailed above where more than two components can be connected to the stimulator unit (or any other unit having the feedthrough teachings detailed herein), connector 1232 as a connector for another unit. In an exemplary embodiment, connector 1232 is a connector of an implantable microphone. In this regard, FIG. 13B depicts an exemplary embodiment of a totally implantable hearing prosthesis. Here, the hearing prosthesis is a middle ear implant hearing prosthesis, where the stimulator assembly 1319 is a DACS actuator that attaches to the outside of the cochlear or to a bone of the middle ear to impart movement onto the oval window or another part of the cochlear to artificially replicate the movement of the bones of the middle ear that in turn moves the portion of the cochlea in a normal hearing person. It is noted that in an exemplary embodiment, the stimulating assembly can be a so-called vibrator of a bone conduction device. (While the embodiment of FIG. 13B is a hearing prosthesis, the teachings detailed herein are applicable to other types of prostheses, such as, for example, a visual prosthesis, where the housing including feedthrough(s) is in signal communication with a stimulating assembly of a retinal implant. In other embodiments, the stimulating assembly is that of a pacemaker. Any stimulating assembly can be utilized in at least some exemplary embodiments.

Still, with respect to FIG. 13B, which depicts a totally implantable hearing prosthesis that includes a stimulating assembly 1319 in the form of a DACS actuator, the hearing prosthesis further includes an implantable microphone 1350. In this embodiment, the stimulating assembly and the implantable microphone are in signal communication with the electronics assembly located in stimulator unit 1322 via the same feedthrough or via separate respective feedthroughs. It is noted that the embodiment of FIG. 13B depicts a configuration where the feedthrough(s) are located on the bottom of the housing, and a feedthrough is also located on a side of the housing. It is noted that in some embodiments, all of the feedthroughs are located on the bottom of the housing. The embodiment of FIG. 13B is presented to show that the various configurations of feedthrough locations can be combined in some embodiments. Still further, in some exemplary embodiments, the housing can include feedthroughs located on two or more sides of the housing (e.g., one as depicted in FIG. 13B, and one on the wall 90 degrees from the one which has feedthrough 513 (with respect to FIG. 13B)). Any arrangement that can enable the teachings detailed herein can be utilized in some embodiments. Again, as noted above, in an exemplary embodiment, the feedthrough(s) can be located on the bottom of the housing and/or on the top of the housing. In the embodiment of FIG. 13B, the stimulating assembly in the implantable microphone or in signal communication with the electronics assembly within the housing via the same feedthrough or via two or more feedthroughs.

In view of the above, it is to be understood that in an exemplary embodiment, there is a device is hermetically sealed and is implantable, which includes a housing. The housing contains circuitry of a hearing prosthesis, and corresponds to the housing detailed above or variations thereof having opening(s) in which feedthrough assembly(ies) are located in the opening(s). The housing also contains a battery. With respect to an axis normal to the length and the width (where the height is the smallest dimension), a plane normal to the axis extends through at least a portion of the feedthrough assembly and through at least a portion of the battery. In this regard, in an exemplary embodiment, a portion of the feedthrough assembly is on the same plane as a portion of the battery. This is depicted by way of example in FIG. 14, where a series of planes (represented by lines 1499, where the planes extend in and out of the page of FIG. 14) that are normal to the axis 1498 (the axis normal to the length and the width) extends through one (actually both) of the feedthroughs and through battery 1050 (where the bottom of the battery is depicted in dashed lines to represent the fact that the wall 842 eclipses that bottom portion).

Figure 14:
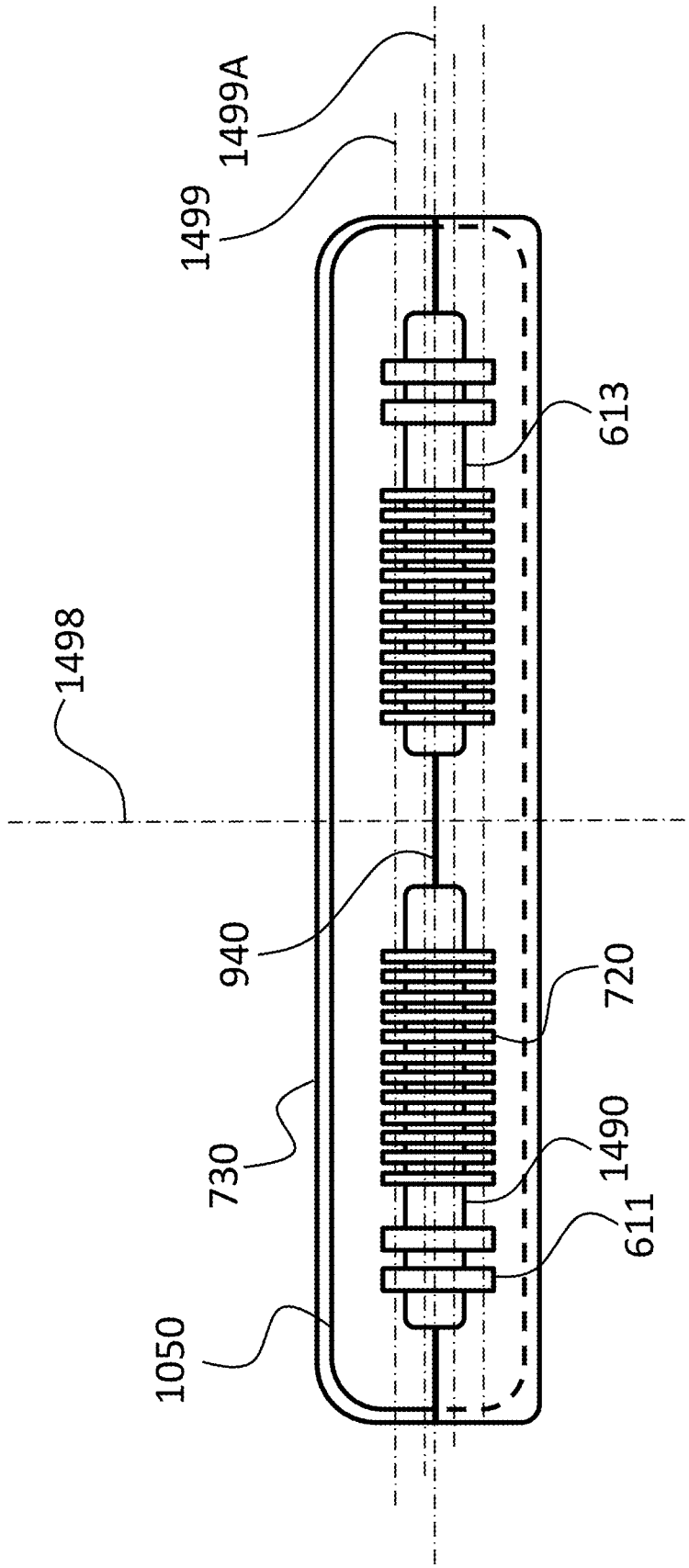

While the embodiment of FIG. 14 is depicted as showing two planes that only extend through the contacts of the feedthroughs, there are also two planes depicted that extend through both contacts and the ceramic body 1490 of the feedthroughs. Thus, in some exemplary embodiments, the aforementioned defined planes extend through both a portion of the ceramic body of the feedthrough and a portion of the battery. This as opposed to the planes just extending through the contacts.

As can be seen, a plane normal to the axis 1498 passes through the geometric center of a feedthrough assembly extends through the portion of the battery (this is plane 1499A). It is noted that in an exemplary embodiment, there is a plane that passes through the geometric center of the ceramic body of the feedthrough assembly that also extends through a portion of the battery. It is also noted that all references to the ceramic body correspond to a disclosure of any other insulator body that can be utilized to insulate the contacts of the feedthroughs from each other and also support a plurality of contacts. In this regard, in an exemplary embodiment, these bodies are monolithic components through which the contacts extend.

Also as can be seen, a plane normal to the axis 1498 that passes through the geometric center of the battery extends through a portion of the feedthrough (again, this is plane 1499A, although this could be another of the planes if the battery was positioned lower or higher than that depicted in FIG. 14). It is noted that in an exemplary embodiment, this plane passes through the ceramic body of the feedthrough assembly. (It is noted that in an exemplary embodiment, the plane passes through both the geometric center of the battery and the geometric center of the feedthrough (and, in some embodiments, the geometric center of the ceramic body of the feedthrough). It is further noted that in some embodiments, the aforementioned planes extend about/almost through the geometric centers just detailed (the planes can extend through the geometric center of one of the components just detailed, and can extend through another component about/almost at the geometric center thereof). In an exemplary embodiment, instead of passing through exactly the geometric centers, with respect to distance normal to the plane, the plane passes through the components at a location within 1%, 2%, 3%, 4%, 5%, 6%, 7%, 8%, 9%, 10%, 11%, 12%, 13%, 14%, 15%, 17.5%, 20%, 22.5%, 25%, 30%, 35%, 40%, or 50% of a distance from the geometric center, where that percentage is measured as a percentage of the total distance along that axis from the bottom to the top of the component. Note further that while the aforementioned arrangement has been described in terms of a range "within" those values, in an alternate embodiment, the planes extend at those values or any range of values therebetween in 0.1% increments (e.g., at 12.4%, 14.4%, 8.5% to 12.7%, etc.). Accordingly, in an exemplary embodiment, a plane normal to the axis and passing through a geometric center of the feedthrough assembly (and, in some embodiments, through the geometric center of the ceramic body) extends through the portion of the battery at a location at least almost at a geometric center of the battery, or vice versa (the plane extending through a portion of the battery at a location at the geometric center of the battery extends through a portion of the feedthrough assembly at a location at least almost at the geometric center of the feedthrough assembly (or ceramic body).

Consistent with the teachings detailed above with respect to the location of the feedthroughs, in an exemplary embodiment, there is a feedthrough assembly located at an axial center of the housing. Also consistent with the teachings detailed above, electronics of a receiver unit of a hearing prosthesis can be located in the housing which has opening(s) through which feedthroughs extend. In this regard, it is noted that the term stimulator unit as detailed herein does not exclude receiver features thereof. That is, in an exemplary embodiment, a stimulator unit 622 is also a stimulator—receiver unit as that unit is known in the art of cochlear implants.

As noted above, in some embodiments, the bottom surface of the housing is a complex surface extending on a first plane and then on a second plane above, with respect to an axis normal to the length and the width, the first plane and then on a third plane below, with respect to the axis, the second plane (thereby establishing the channel for the connectors of the components to be attached to the stimulator unit, etc.). In some embodiments, the second plane extends through the battery (e.g., the plane established by wall 940/the plane on which wall 940 extends through a portion of the battery). Consistent with the teachings detailed above, this second plane includes the opening in the housing (the opening through which the feedthrough extends).

Figure 15B:
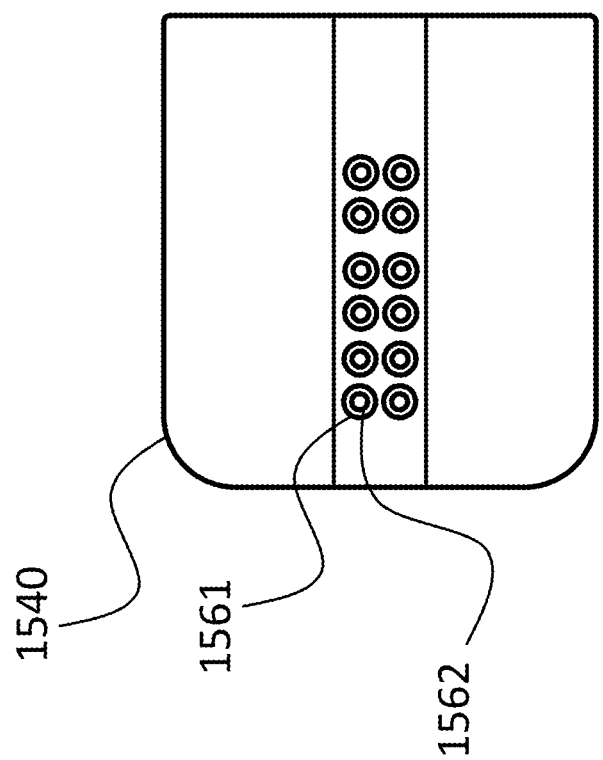

FIG. 15A depicts an exemplary embodiment of a housing 1530 having an opening therein with a single feedthrough 1555 where the feedthrough 1555 is centered in the housing (with respect to the plane of FIG. 15) and is symmetrically located about a center of the length and width of the housing 1530. FIG. 15B depicts an alternate exemplary embodiment of a housing 1540 that includes through holes for each individual conductor 1562, where each conductor 1562 is surrounded by an insulator 1561, which is press-fit or brazed or otherwise bonded through each of the hole through the housing. In this regard, each conductor 1562 has its own separate insulator body, which is monolithic. By way of example only and not by way of limitation, glass beads can correspond to the insulator, and the conductor can be a platinum wire or rod or the like.

It is noted that the embodiments of FIGS. 15A, 15B, and 7 depicts an exemplary embodiment of an implantable component including a feedthrough, where the feedthrough closes an opening in a housing. With respect to FIGS. 7 and 15B, there are a plurality of feedthroughs (2 in FIG. 7, and 12 in FIG. 15B), and with respect to FIG. 15A, there is only one feedthrough. With respect to FIG. 15A, a single insulator (a monolithic insulator) is utilized to insulate all of the electrical conductors from each other and from the housing, whereas with respect to FIGS. 15B and 7, a plurality of insulators are utilized (FIG. 15B utilizes a separate insulator for each conductor, and FIG. 7 utilizes two separate insulators, wherein the conductors are arrayed within those two separate insulators). With respect to FIGS. 7, 15A, and 15B, it can be seen that the implantable device includes a plurality of feedthrough conductors, wherein the conductors are arranged in a linear matter. With respect to FIG. 15B, any one feedthrough includes a conductor that is a part of the plurality of feedthrough is including a conductor Still with reference to an implantable device that includes an implantable hermetically-sealed housing of a hearing prosthesis, the housing having an opening and a feedthrough assembly being located in the housing, and a battery assembly located in the housing, in an exemplary embodiment, the battery assembly provides structural reinforcement to the housing. Accordingly, in an exemplary embodiment, there is a device that includes a plurality of feedthroughs, such as 12 feedthroughs, each of the feedthroughs having a respective conductor, and the 12 conductors are arranged in a linear manner (here, two lines of 6 conductors).

Elements 1561 and 1562 in combination form a feedthrough assembly, just as is the case with respect to the insulator body in combination with the conductors of feedthroughs 611.

The embodiments of FIGS. 7, 15A, and 15B depict a plurality of feedthrough conductors arranged in an elongate manner wherein the feedthrough conductors extend through the housing. With respect to the embodiment of FIG. 12, where the body of the feedthrough includes conductors arranged in a manner akin to that of FIG. 7, the plurality of feedthrough conductors arranged in an elongate manner are generally aligned with the longitudinal axis of the implantable medical device.

Figure 16:
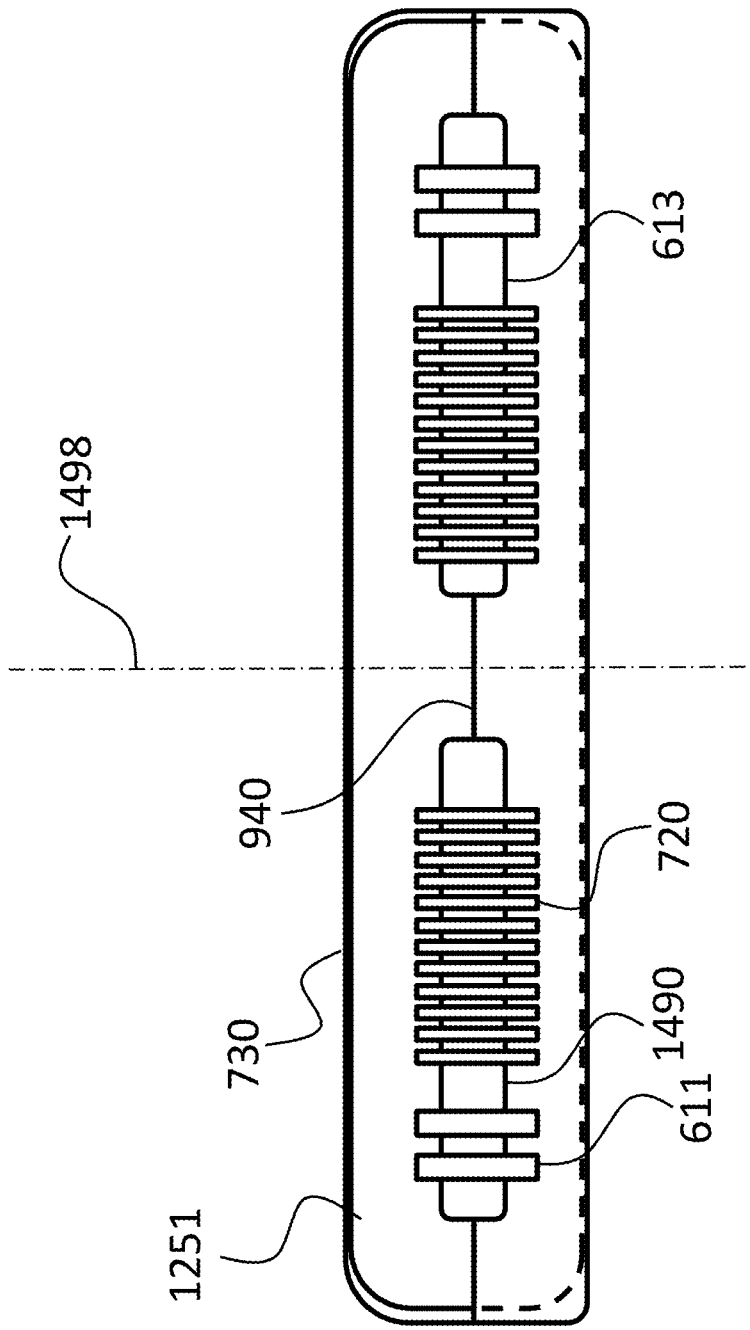

FIG. 16 depicts such an exemplary embodiment, where battery assembly 1251 is shown in the housing 730, where a portion thereof is eclipsed by the vertical wall of the housing forming the channel (which portion is represented by dashed lines). As can be seen, the housing and the battery assembly are sized and dimensioned such that there is relatively little space between the top of the battery assembly 1251 and the interior surface of the top wall of the housing 730. Also as can be seen, the housing and the battery assembly are sized and dimensioned such that there is relatively little space between the bottom of the battery assembly 1251 and the interior surface of the bottom wall of the housing 730 (the wall that forms surface 799). Because of this feature, a compressive force applied on to the top or bottom of the housing 730 (e.g., one parallel to axis 1498) that would cause the housing 730 to deflect a relatively significant amount relative to its static unloaded position can be resisted by the battery assembly 1251 when the housing 730 is deflected, so as to come into contact with battery assembly 1251. Note also that in some embodiments, battery assembly 1251 is in direct contact with the housing 730 without deformation, while in other embodiments, a frame or some other spacer structure is located between the battery assembly 1251 and the housing such that there is a structural material path between the housing and the battery assembly 1251 in the vertical direction. Note further that in some exemplary embodiments, the arrangement of the housing 730 and the battery assembly 1251 (and other components that may be present) is such that the battery assembly 1251 creates an expansive force on the housing 730. In this regard, in an exemplary embodiment, the housing and the battery assembly and other components thereof can be sized and dimensioned such that a compressive force was to be applied onto the housing 730 to hermetically seal device because of the dimensions and size of the battery assembly 1251. Thus, the housing is somewhat "preloaded" to resist compression. This is somewhat of the inverse or opposite concept of "pre-stressed concrete." In any event, irrespective of the specific arrangement of the housing and the battery assembly 1251, in an exemplary embodiment the battery assembly provides structural reinforcement to the housing.

FIGS. 17 and 18 provide additional details of an arrangement where the battery assembly provides structural reinforcement to the housing. As can be seen, battery assembly 1251 includes a first shell component 1252 and a second shell component 1254 that are connected to each other via frame 1253. Frame 1253 extends about battery 1050. The shell components are welded or otherwise connected to the frame 1253 to form an insulated and/or pressurized (or at least pressure resistant) or gas impermeable barrier between the battery 1050 and the interior of the housing 1030. As seen in the figures above, the battery 1050 is an elongate tube having a racetrack outer cross-section. FIG. 18 also depicts the conductor 1255 that is used to conduct current from inside the barrier established by the shells 1252 and 1254 to the outside.

As can be seen, the battery assembly has a top major side and a bottom major side extending parallel to a longitudinal axis of the battery assembly (as opposed to the minor sides that include the frame 1253 that also extend parallel to the longitudinal axis) where, when placed in the housing and the housing is closed, respectively abuts a top and a bottom housing wall of the housing, thereby structurally reinforcing the housing. As can be seen, in some embodiments the shells include structure 1861 that extends from the flat surfaces of the shells, which, in some embodiments, constitutes the structure that contacts the housing walls. In other embodiments, the respective major sides are flat without structure 1861. As can be seen, structure 1861 can be made by stamping the shells or vacuum forming or molding, etc., so as to deform to have these structures 1861. It is noted that in at least some exemplary embodiments, the structures 1861 provide additional strengthening of the shells in the direction normal to the longitudinal axis. It is also noted that in some exemplary embodiments, structures 1861 can run parallel to the longitudinal axis as well, thereby providing additional strengthening of the shell in the direction of the longitudinal axis. Again, it is noted that in at least some embodiments, there is a space between the shells and the housing.

As can be seen in FIG. 18, with respect to the axis normal to the length and the width of the housing 730, the feedthrough(s) is entirely located below a top of the battery assembly and above a bottom of the battery assembly, and entirely located below a top of the battery and above a bottom of the battery. That said, in an exemplary embodiment, the feedthroughs are (i) located entirely below a top of the battery assembly and/or battery or (ii) located entirely above a bottom of the battery assembly and/or battery (but not both).

In an exemplary embodiment, the stimulator unit is configured such that upon a collapse of the housing in a direction normal to the length and the width, the battery will be destroyed before the feedthrough is destroyed, where the word "destroyed" means that, with respect to an implanted stimulator unit, explanation of the unit would be required due to the state of the battery or the feedthrough vis-à-vis if functionality of such component at pre-collapse standards is desired.

Briefly, it is noted that the housings detailed herein can be housings having a length dimension L, a width dimension W, and a height dimension H, wherein L and W are variously equal to or less than 35 mm, 34, 33, 32, 31, 30, 29, 28, 27, 26, 25, 24, 23, 22, 21, 20, 19, 18, 17, 16, 15, 14, 13, 12, 11, or 10 mm or any value or range of values therebetween in 0.1 mm increments (e.g., L could be 30 mm, and W could be 24.3 mm or less than those values), and H is any value equal to or less than 15 mm, 14, 13, 12, 11, 10, 9, 8, 7, 6, 5, 4, or 3 mm or any value or range of values therebetween in 0.1 mm increments.

In an exemplary embodiment, the housing includes a receiver-stimulator assembly. By way of example only and not by way of limitation, the PCB 1261 includes a processor 1277 as an integral part thereof or attached thereto, which includes software or has access to software or includes or has access to firmware that analyzes the received signal from the implanted coil and analyzes the signal and develops an output control signal to output to the simulative device (e.g., the electrode array) to stimulate the recipient. In an exemplary embodiment, the receiver-stimulator assembly is a receiver-stimulator of a cochlear implant.

As will be understood by the teachings above, in at least some embodiments, the housing/feedthrough combination is such that the feedthrough is completely recessed relative to the shipping rectangular cuboid of the housing. By shipping rectangular cuboid, it is meant a cuboid (6 sided volume having rectangular shapes—square or non-square) where a length, a width and a height is no greater than that which is required to entirely encompass the housing (e.g., if one were to ship the housing (or stimulator unit 622), the smallest size interior of a box would be this shape, hence shipping cuboid). Because of the designs of some of the embodiments, the feedthrough is not a driver of the shipping cuboid.

In an exemplary embodiment, the battery assembly is configured to limit a deflection of the housing inward for a given load at a point location where the housing extends over the battery assembly to no more than ABC percent of that which would otherwise be the case, all other things being equal. In an exemplary embodiment, ABC is 50%, 40%, 35%, 30%, 25%, 20%, 15%, 10%, 9, 8, 7, 6, 5, 4, 3, 2 or 1% or 0.5% or 0.25% or less or any value or range of values therebetween in 0.05 percent increments. In an exemplary embodiment, this is the case with respect to a point location that would have exhibited the most deformation with respect to a given load applied at that point (e.g., a point away from the vertical walls of the housing will deflect more than a point closer to the vertical walls, all other things being equal). In an exemplary embodiment, the battery assembly is configured to limit a deflection of the housing inward for a given load at a point location irrespective of location over the battery assembly to no more than ABC percent of that which would otherwise be the case. By way of example only and not by way of limitation, the point location can be directly over one of the feedthroughs, or at a location in between the two feedthroughs. In an exemplary embodiment, the battery assembly is configured to limit a deflection of the housing inward for a given load by an average amount (average of all points of the top of the housing) by ABC percent relative to that which would be the case in the absence of the battery assembly, all other things being equal. In an exemplary embodiment, the average is a mean. In an exemplary embodiment, the average is a median. In an exemplary embodiment, the average is a mode. In an exemplary embodiment, the battery assembly is configured to limit the flexion of the housing inward at a point location where such is greatest for a given load by ABC percent, all other things being equal. In an exemplary embodiment, this location where the deflection is the greatest can be the center of the top wall (because it is furthest from the vertical walls).

In an exemplary embodiment, the load is 1, 2, 3, 4, 5, 6, 7, 8, 9, 10, 12, 14, 16, 18, 20, 22, 24, 26, 28, 30, 32, 34, 35, 38, 40, 45, 50, 55, 60, 65, 70, 75, 80, 85, 90, 95, 100, 110, 120, 130, 140, 150, 160, 170, 180, 190, or 200 pounds over an area of 1 cm by 1 cm or any value or range of values therebetween in 0.1 pound increments. In an exemplary embodiment, the load is an impact load of 0.01, 0.025, 0.05, 0.1, 0.15, 0.2, 0.25, 0.3, 0.35, 0.4, 0.45, 0.5, 0.55, 0.6, 0.65, 0.7, 0.8. 0.9. 1.0, 1.1, 1.2, 1.3, 1.4, 1.5, 1.75, 2, 2.25, 2.5, 2.75, 3, 3.5, 4, 4.5, 5, 5.5, 6, 6.5, 7, 7.5, 8, 9, 10, 11, 12, 13 Jules over the 1 cm by 1 cm area or any value or range of values therebetween in 0.01 joule increments.

In an exemplary embodiment, the battery assembly has a top major side and a bottom major side, which sides extend parallel to a longitudinal axis thereof, wherein the top major side or a bottom major side or both are respectively located 0.1 mm or less, 0.2 mm or less, 0.3, 0.4, 0.5, 0.6, 0.7, 0.8, 0.9, 1.0, 1.1, 1.25, 1.5, 1.75, or 2 mm or less or any value or range of values therebetween in 0.01 mm increments from, respectively, a top housing wall or a bottom housing wall, thereby structurally reinforcing the housing.

In an exemplary embodiment, there is a device, comprising: a housing of a hearing prosthesis, the housing having an opening; a battery located in the housing; and a feedthrough assembly located in the opening, wherein the housing has a length, a width, and a height, the height being the smallest dimension, wherein with respect to an axis normal to the length and the width, a plane normal to the axis extends through at least a portion of the feedthrough assembly and through at least a portion of the battery, the device is hermetically sealed, and the feedthrough assembly establishes a portion of the hermetic seal.

In an exemplary embodiment, there is a device as described above and/or below, wherein a bottom surface of the housing is a complex surface extending on a first plane and then on a second plane above, with respect to an axis normal to the length and the width, the first plane and then on a third plane below, with respect to the axis, the second plane; and the second plane extends through the battery.

In an exemplary embodiment, there is a device as described above and/or below, wherein the second plane includes the opening.

In an exemplary embodiment, there is an implantable medical device comprising a housing; an induction coil; and a plurality of feedthrough conductors arranged in an elongate manner, the feedthrough conductors extending through the housing, wherein the implantable medical device has a longitudinal axis that extends through a geometric center of the induction coil, and wherein the plurality of feedthrough conductors arranged in an elongate manner are generally aligned with the longitudinal axis of the implantable medical device.

In an exemplary embodiment, there is a device as described above and/or below, wherein the induction coil is disposed beside a first end of the housing and connected to at least one of the conductors of the plurality of conductors, and the longitudinal axis bisects the first end of the housing. In an exemplary embodiment, there is a device as described above and/or below wherein: the induction coil is disposed beside a first end of the housing. the implantable medical device comprises an electrical lead that extends from a second end of the housing, and the longitudinal axis intersects the second end of the housing with respect to a top view thereof at least at the same general location as the electrical lead. In an exemplary embodiment, there is a device as described above and/or below, wherein the first and second ends are opposite ends of the housing. In an exemplary embodiment, there is a device as described above and/or below, wherein the housing comprises first and second opposing major faces, and the plurality of feedthrough conductors are recessed in one of the first or second opposing major surface in an electrically insulated manner from the material of the housing. In an exemplary embodiment, there is a device as described above and/or below, wherein at least one plate electrode is disposed generally co-planar with the other of the first and second opposing major surfaces and generally aligned with the longitudinal axis of the implantable medical device. In an exemplary embodiment, there is a device as described above and/or below, the housing is device sealed, an electronic assembly is disposed in the housing on one side of the longitudinal axis, and a battery is disposed in the housing on the other side of the longitudinal axis.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system.

Any feature of any embodiment can be combined with any other feature any other embodiment providing that such is enabled.

It is noted that in at least some exemplary embodiments, any feature disclosed herein can be utilized in combination with any other feature disclosed herein unless otherwise specified. Accordingly, exemplary embodiments include a medical device including one or more or all of the teachings detailed herein, in any combination.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A hearing prosthesis, comprising:
   a hermetically sealed housing containing electronics for the hearing prosthesis; and
   a battery, wherein
   the housing comprises a top wall and bottom wall, the housing having a length, a width, and a height, wherein the height is the smallest dimension and is established by the top and bottom walls,
   the housing establishes a channel, the channel being formed by portions of the bottom wall which extend upwards, the channel extending from one side to the other side of the housing,
   the housing has an opening which opens into the channel,
   the hearing prosthesis includes a feedthrough assembly extending in the opening, establishing a portion of the hermetic seal,
   the battery is located in the housing,
   a plane normal to the height of the housing extends through at least a portion of the feedthrough assembly and through at least a portion of the battery,
   the hearing prosthesis further comprises a stimulator assembly external to the housing, and
   the stimulator assembly is a vibrator of a bone conduction device or an actuator of a direct acoustic cochlear stimulator or a cochlear implant electrode array.

2. The hearing prosthesis of claim 1, wherein:
   the stimulator assembly is located outside the housing and is in electrical signal communication with the electronics via the feedthrough assembly.

3. The hearing prosthesis of claim 2, wherein:
   the stimulator assembly is the vibrator of a bone conduction device.

4. The hearing prosthesis of claim 2, wherein:
   the stimulator assembly is the actuator of a direct acoustic cochlear stimulator.

5. The hearing prosthesis of claim 1, wherein:
   the electronics are electronics of a control unit for at least one of:
   an active transcutaneous bone conduction device; or
   a middle ear implant.

6. The hearing prosthesis of claim 5, wherein:
   the electronics are for a control unit of a middle ear implant.

7. The hearing prosthesis of claim 1, wherein:
   a plane normal to the axis and passing through a geometric center of the battery extends through the portion of the feedthrough assembly.

8. The hearing prosthesis of claim 1, wherein:
   a plane normal to the axis and passing through a geometric center of the feedthrough assembly extends through the portion of the battery at a location at least almost at a geometric center of the battery.

9. The hearing prosthesis of claim 1, wherein:
   a bottom surface of the housing is a complex surface extending on a first plane and then on a second plane above, with respect to an axis normal to the length and the width, the first plane and then on a third plane below, with respect to the axis, the second plane, the complex surface establishing the channel; and
   the second plane extends through the battery.

10. The hearing prosthesis of claim 1, wherein:
    the top wall and bottom wall of the housing are defined by faces that directly face planes that are normal to the height of the housing.

11. The hearing prosthesis of claim 1, wherein:
    the hearing prosthesis is a stimulator implant or a receiver-stimulator implant of a cochlear implant.

12. The hearing prosthesis of claim 1, wherein:
    the height is no more than $\frac{1}{4}$ of the length and no more than $\frac{1}{4}^{th}$ of the width.

13. The hearing prosthesis of claim 1, wherein:
    with respect to a view looking down on a plane established by the length and the width, the electronics are located on a first side of the housing, the battery is located on a second, opposite side of the housing, and the feedthrough assembly is located between the battery and at least most of the electronics.

14. The hearing prosthesis of claim 1, wherein:
the feedthrough assembly is located in at least about the center of at least one of the length or the width.

15. The hearing prosthesis of claim 1, wherein:
with respect to a view looking down on a plane established by the length and the width, at least one of the battery or the electronics does not overlap the feedthrough assembly.

16. The hearing prosthesis of claim 1, wherein:
the hearing prosthesis is a totally implantable hearing prosthesis that includes an implantable microphone; and
the stimulating assembly and the implantable microphone are in signal communication with the electronics via the feedthrough assembly or via respectively the feedthrough assembly and one or more other feedthrough assemblies.

17. The hearing prosthesis of claim 1, wherein:
with respect to a view looking down on a plane established by the length and the width, the battery is located on a first side of the housing, and the feedthrough assembly is located adjacent the battery in a non-overlapping manner.

18. The hearing prosthesis of claim 1, wherein:
with respect to the axis normal to the length and the width, a first ECE (extra-cochlea electrode) plate is located above the opening, and a second ECE plate is located above a second opening.

19. The hearing prosthesis of claim 1, wherein:
a bottom of the housing is a complex surface that extends from a first side on a first plane, and then extends on a second plane above the first plane and then extends on a third plane below the second plane, the complex surface being the channel; and
the space between the second plane and the first plane provides a clearance between tissue of a recipient of the hearing prosthesis supporting the hearing prosthesis and interfacing with the housing extending on the first plane and a lead assembly electrically coupled to the feedthrough assembly, wherein
the bottom extends normal to an axis normal to the length and the width.

20. The hearing prosthesis of claim 1, wherein:
the battery extends in the height direction a substantial amount of an interior height of the housing.

21. The hearing prosthesis of claim 1, wherein:
the battery extends in the width direction a majority of an interior width of the housing.

22. The hearing prosthesis of claim 1, wherein:
the electronics are for a control unit of an active transcutaneous bone conduction device.

23. The hearing prosthesis of claim 1, wherein:
the hearing prosthesis includes an inductance coil;
the stimulator assembly is located outside the housing and is in electrical signal communication with the electronics via the feedthrough assembly.

24. The hearing prosthesis of claim 1, wherein:
the stimulator assembly is in electrical signal communication with the electronics via the feedthrough assembly.

25. The hearing prosthesis of claim 1, wherein:
the stimulator assembly is located outside the housing and is in electrical signal communication with the electronics via the feedthrough assembly, wherein the stimulator assembly is the cochlear implant electrode array.

26. The hearing prosthesis of claim 1, wherein:
the hearing prosthesis is an implantable portion of a cochlear implant.

27. The hearing prosthesis of claim 1, wherein:
the hearing prosthesis is an implantable portion of a cochlear implant.

* * * * *